(12) United States Patent
Chen et al.

(10) Patent No.: US 9,944,901 B2
(45) Date of Patent: Apr. 17, 2018

(54) FUSION PROTEIN FOR INDUCING PLURIPOTENT STEM CELLS AND APPLICATION METHOD THEREOF

(71) Applicants: Institute of Zoology, Chinese Academy of Sciences, Beijing (CN); Emory University School of Medicine, Atlanta, GA (US)

(72) Inventors: Dahua Chen, Beijing (CN); Peng Jin, Atlanta, GA (US); Qinmiao Sun, Beijing (CN); Weiqi Tan, Beijing (CN)

(73) Assignees: Institute of Zoology, Chinese Academy of Sciences, Beijing (CN); Emory University School of Medicine, Atlanta, GA (US)

( * ) Notice: Subject to any disclaimer, the term of this patent is extended or adjusted under 35 U.S.C. 154(b) by 0 days.

(21) Appl. No.: 15/111,483

(22) PCT Filed: Jun. 17, 2014

(86) PCT No.: PCT/CN2014/080042
§ 371 (c)(1),
(2) Date: Jul. 14, 2016

(87) PCT Pub. No.: WO2015/106535
PCT Pub. Date: Jul. 23, 2015

(65) Prior Publication Data
US 2016/0348077 A1  Dec. 1, 2016

(30) Foreign Application Priority Data

Jan. 16, 2014  (CN) .......................... 2014 1 0020902

(51) Int. Cl.
| | | |
|---|---|---|
| *C12N 5/07* | (2010.01) | |
| *C12N 5/074* | (2010.01) | |
| *C12N 15/62* | (2006.01) | |
| *C12N 15/86* | (2006.01) | |
| *C07K 14/47* | (2006.01) | |
| *C12N 7/00* | (2006.01) | |
| *C12Q 1/68* | (2018.01) | |

(52) U.S. Cl.
CPC ........ *C12N 5/0696* (2013.01); *C07K 14/4702* (2013.01); *C12N 7/00* (2013.01); *C12N 15/86* (2013.01); *C12Q 1/6881* (2013.01); *C07K 2319/71* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2506/02* (2013.01); *C12N 2740/10043* (2013.01); *C12N 2740/10052* (2013.01); *C12N 2740/13043* (2013.01)

(58) Field of Classification Search
CPC .............. C12N 15/86; C12N 2501/602; C12N 2501/603; C12N 2501/604; C12N 2501/605; C12N 2506/45; C12N 2740/10052; C12N 5/0696; C07K 2319/71
USPC ...................................... 435/377, 320.1, 456
See application file for complete search history.

(56) References Cited

U.S. PATENT DOCUMENTS

| | | | | |
|---|---|---|---|---|
| 2012/0115225 A1* | 5/2012 | Xu | ........................ | C12N 5/0696 435/366 |
| 2013/0065814 A1* | 3/2013 | Xu | ........................ | C07K 14/52 514/1.1 |

FOREIGN PATENT DOCUMENTS

| | | | |
|---|---|---|---|
| CN | 101457225 | * | 6/2009 |
| CN | 101457225 A | | 6/2009 |
| CN | 102190731 A | | 9/2011 |
| CN | 103739718 A | | 4/2014 |
| WO | WO 2011/110051 | * | 9/2011 |

OTHER PUBLICATIONS

Uniprot Accession No. P46938 (Q52KJ5) (Q91WL1), Mouse YAP1, integrated into the database on Nov. 1, 1995.*
Yagi et al. (1999) EMBO J., vol. 18(9), 2551-2562.*
State Intellectual Property Office of the People's Republic of China (ISR/CN), International Search Report for PCT/CN2014/080042, China, Sep. 16, 2014.
Kamachi, Y. et al., Mechanism of regulatory target selection by the SOX high-mobility-group domain proteins as revealed by comparison of SOX1/2/3 and SOX9, Molecular and Cellular Biology, Jan. 1999, vol. 19, No. 1, pp. 107-120.
Wang, Z. et al., Aromatic residues in the C-terminal domain 2 are required for Nanog to mediate LIF-independent self-renewal of mouse embryonic stem cells, Journal of Biological Chemistry, Dec. 17, 2007, vol. 283, No. 8, pp. 4480-4489.
Lunde, K. et al., Zebrafish pou5f1/pou2, homolog of mammalian Oct4, functions in the endoderm specification cascade, Current Biology, Jan. 6, 2004, vol. 14, pp. 48-55.
Lian, I. et al., The role of YAP transcription coactivator in regulating stem cell self-renewal and differentiation, Genes & Development, Dec. 31, 2010, vol. 24, pp. 1106-1118.

* cited by examiner

*Primary Examiner* — Anne Marie S Wehbe
(74) *Attorney, Agent, or Firm* — Shuang Chang; PSK Intellectual Property Group, LLC

(57) ABSTRACT

Provided is a protein coded by a gene related to cell totipotency and a transcriptional activation domain of a mammalian YAP protein or a fusion protein of a segment with a transcriptional control activity, a coding nucleotide sequence, an expression vector and a composition thereof, as well as a method for inducing the pluripotent stem cells by using the fusion protein.

4 Claims, 5 Drawing Sheets

FUSION PROTEIN FOR INDUCING PLURIPOTENT STEM CELLS AND APPLICATION METHOD THEREOF

CROSS-REFERNCE TO RELATED APPLICATIONS

This application is a U.S. national phase application of PCT Patent Application Serial No. PCT/CN2014/080042, filed on Jun. 17, 2014, and claims priority to and benefit of Chinese Patent Application No. 201410020902.1, filed on Jan. 16, 2014 in the State Intellectual Property Office of P.R. China, which are incorporated herein by reference in their entireties.

TECHNICAL FIELD

The present invention relates to the field of pluripotent stem cells. Specifically, the present invention relates to an artificial transcription factor for reprogramming somatic cells into pluripotent stem cells, and a use thereof in somatic cell reprogramming. The present invention further relates to a method for reprogramming somatic cell into induced pluripotent stem cells.

BACKGROUND

Embryonic stem cells are a group of undifferentiated totipotential cells derived from inner cell mass of early development stage embryo in fertilized ovum or from primordial germ cells after embryo implantation, have unlimited multiplication and differentiation potential, and can be differentiated into cells of almost all histologic types. Hence, they have a broad prospect in aspects of animal cloning, fundamental research of development biology, especially human regenerative medicine. However, there are still many difficulties in really using embryonic stem cells in clinic; specifically, the resource of human embryonic stem cells especially patient-specific stem cells and related ethical issues are serious challenges in scientific community. Hence, it is an objective pursued and struggled by many researchers to obtain pluripotent cells similar to embryonic stem cells from undifferentiated cells by using abundant somatic cells via reprogramming methods.

So far, there are mainly three techniques for obtain stem cells by inducing reprogramming in somatic cells: somatic cell nuclear transfer reprogramming (SCNT), cell fusion reprogramming and induced pluripotent stem cell reprogramming (iPS). In 1952, nuclear transfer was firstly obtained successfully in amphibians (Briggs and King, 1952), the clone sheep Dolly was born in 1997 (Wilmut et al., 1997), and somatic cell cloning technique rapidly developed and gradually matured. So far, somatic cell cloning has been successfully implemented in more than 20 animals such as rats, pigs, bovines, monkeys and dogs. Stem cells obtained by nuclear transfer can avoid adverse reactions such as immunological rejection after cell transplantation therapy.

However, this technique still has many problems in real clinical applications. Firstly, nuclear transfer has a very low efficiency; secondly, some experiments confirm that somatic cell cloning animals frequently have abnormal development problem; and sources of human ovum and use of human embryo associated to final applications in treatment of human diseases are still in ethical controversy. All these are bottleneck problems for this technique. Similarly, cell fusion reprogramming technique also faces many problems such as very low reprogramming efficiency, too high requirement in technology, which restrict the clinical applications thereof. Both of the above two conventional reprogramming methods have drawbacks, so that many scientists in the world are exploring other more feasible reprogramming strategies. In 2006, the research group of Japan scientist Yamanaka found that 4 transcription factors Oct4, Sox2, Klf4 and c-Myc could be transferred into mouse fibroblasts via viral infection, then the obtained fibroblasts had pluripotency similar to that of ES cells (Takahashi and Yamanaka, 2006). The subsequent researches showed that such induced pluripotent stem cells (iPS cells) were very similar to embryonic stem cells and could form chimeric mice after being injected into blastula. In particular, the birth of mice generated via tetraploid complementation technique in 2009 confirms the pluripotency of this kind of cells. In November of 2007, the laboratories of Yamanaka and Thomson separately declared that they successfully induced human iPS cells by using human skin cells (Takahashi et al., 2007; Yu et al., 2007). In the same year, the research group of Jaenisch achieved primary success in gene therapy by using iPS technique in sickle cell anemia mouse model. In brief, reprogramming and recovery of pluripotency surprisingly occurred in differentiated somatic cells by introducing several simple transcription factors via this technique. This simple but feasible technique breakthrough can conveniently obtain pluripotent stem cells from somatic cells of patients themselves, which not only simply solves the problem of cell sources for regeneration therapy, but also avoids autoimmune rejection, evades ethic restriction, and establishes solid basis for clinical application of regeneration medicine.

However, the technique for inducing pluripotent stem cells as a new technique is imperfect in many aspects. For example, its mechanism is not clear, it may have potential risks in safety, and it has low induction efficiency and a long induction time. If these problems could not be sufficiently solved, this technique cannot be successfully used in clinic. Hence, tremendous efforts have been made to solve these problems, and a lot of progresses have been achieved so far.

Firstly, scientists in the world have made sufficient researches in iPS induction mechanism from aspect of molecular biology and molecular biology. For example, the scientists' articles in terms of single cell level, chromatin modification enzyme and 3D chromatin regulation give us in-depth knowledge of reprogramming mechanism in transcription level, epigenetic level, signal transduction and so on. In particular, the "seesaw model" of Hongkui Deng of Peking University lets us know the iPS mechanism more comprehensively.

Secondly, many improvements have been made in safety of iPS. First of all, c-Myc was removed from the 4 factors so as to significantly reduce risks in tumorigenicity. In addition, more safe induction means, such as use of non-viral integration vectors, mRNA, protein induction means, small molecule induction means of Hongkui Deng, make great improvement in safety of iPS.

Thirdly, conventional iPS has an induction efficiency of about 0.01% to 2%. Thus, many scientists use various methods to improve induction efficiency. For example, the addition of small molecular compounds such as VPA, VC can elevate induction efficiency by about 100 times, and the optimized combination of induction factors such as mRNA induction may elevate the efficiency up to about 5%. Pluripotent factor fused VP16 or transcriptional activation domain of MyoD may also significantly increase iPS induction efficiency.

Fourthly, the iPS induction time for mouse cells is about 2 weeks in general, and the time of human iPS cells is much longer. Thus, it is also a very important factor for final clinical application to obtain iPS in the shortest possible time, but at present, the induction time is usually about 2 weeks.

In the patent application with application number of WO2011110051, OCT4, SOX2, NANOG are separately fused with herpes virus VP16 transcription activation domain. These 3 kinds of artificial transcription factors together with Klf4 infect MEF cells, which may significantly improve reprogramming efficiency. However, this technique still does not achieve ideal conditions in terms of speed and efficiency. For example, the expression of endogenous pluripotent genes such as Oct4 is not fast enough. Hirai et al. fused OCT4 and MyoD transcription activation domain, then the MyoD-fused OCT4 as an artificial factor (M30) together with three transcription factors, SOX2, c-Myc, Klf4 in primitive form are used to infect MEF cells, the reprogramming efficiency was significantly elevated. GFP positive clone count result showed this method for inducing pluripotent stem cells could achieve the highest value of GFP positive clone on the day 15, and the induction efficiency was up to about 25%, which was about 10 times that of conventional Oct4, SOX2, c-Myc, Klf4 induction method. In the meantime, this method still uses proto-oncogene c-Myc, and thus cannot avoid potential safety risk. In comparison, the present invention has higher safety, higher efficiency, and shorter induction time. Thus, the present invention is more promising in regenerative medicine clinic application in future.

Although the researches of iPS have achieved considerable progresses in the past several years and its glorious prospect in final clinical uses is gradually revealed to us, the technique in general still has problems such as in low induction efficiency, long time, and safety problem, which impede rapid and efficient acquisition of high quality iPS cells for clinical application.

CONTENTS OF THE INVENTION

Therefore, the objective of the present invention is to provide a method for safely, rapidly and efficiently inducing and producing pluripotent stem cells to overcome drawbacks such as low induction efficiency (0.01% to 2%) and long time (about 10 days to about 2 weeks) generally existed in various method for inducing and producing iPS in the prior art, and the method provides a basis for clinical application of iPS.

In one aspect, the present invention provides a fusion protein, the fusion protein comprises a protein or fragment thereof encoded by a cell totipotency-related gene, and a transcriptional control domain or fragment thereof having transcriptional control activity which links directly to or links via a linker sequence to the protein or fragment thereof encoded by the cell totipotency-related gene.

Preferably, the linker sequence is GGGGS.

Preferably, the protein or fragment thereof encoded by the cell totipotency-related gene links to the transcriptional control domain or fragment thereof having transcriptional control activity via amino terminal or carboxyl terminal.

Preferably, the cell totipotency-related gene is one or more selected from OCT4, SOX2, NANOG, SOX1, SOX3, SOX15, SOX18, STAT3, SMAD1, Sal4, Nr5a2, Dax1, Esrrb, Utf1, MyoD, CEBPα, Pax5, Pdx1, Ngn3, MafA, Ascl1, Brn2, Myt11, Gata4, Mef2c and Tbx5. More preferably, the cell totipotency-related gene is one or more selected from OCT4, SOX2, NANOG, MyoD, CEBPα, Pax5, Pdx1, Ngn3, MafA, Ascl1, Brn2, Gata4, Mef2c and Tbx5. More preferably, the cell totipotency-related gene is one or more, such as one, two or three, selected from OCT4, SOX2 and NANOG.

Preferably, the transcriptional control domain is a transcriptional activation domain (TAD) of mammal YAP protein or fragment thereof having transcriptional control activity. More preferably, the transcriptional control domain is a transcriptional activation domain of mouse, swine, caprine, bovine or human YAP protein or fragment thereof having transcriptional control activity. Further preferably, the transcriptional control domain is a transcriptional activation domain of mouse YAP protein or fragment thereof having transcriptional control activity, preferably, the amino acid sequence of the transcriptional control domain is set forth in SEQ ID NO: 10.

Preferably, the fusion protein is one or more selected from: a fusion protein formed by fusion of OCT4 protein and YAP protein transcriptional activation domain, i.e., OCT4-YAP$^{TAD}$ (hereinafter cited as Oy); a fusion protein formed by fusion of SOX2 protein and YAP protein transcriptional activation domain, i.e., SOX2-YAP$^{TAD}$ (hereinafter cited as Sy); a fusion formed by fusion of NANOG protein and YAP protein transcriptional activation domain, i.e., NANOG-YAP$^{TAD}$ (hereinafter cited as Ny); a fusion protein formed by fusion of MyoD protein and YAP protein transcriptional activation domain; a fusion protein formed by fusion of CEBPα protein and YAP protein transcriptional activation domain; a fusion protein formed by fusion of Pax5 protein and YAP protein transcriptional activation domain; a fusion protein formed by fusion of Pdx1 protein and YAP protein transcriptional activation domain; a fusion protein formed by fusion of Ngn3 protein and YAP protein transcriptional activation domain; a fusion protein formed by fusion of MafA protein and YAP protein transcriptional activation domain; a fusion protein formed by fusion of Ascl1 protein and YAP protein transcriptional activation domain; a fusion protein formed by fusion of Brn2 protein and YAP protein transcriptional activation domain; a fusion protein formed by fusion of Gata4 protein and YAP protein transcriptional activation domain; a fusion protein formed by fusion of Mef2c protein and YAP protein transcriptional activation domain; a fusion protein formed by fusion of Tbx5 protein and YAP protein transcriptional activation domain.

Preferably, the fusion protein of the present invention is one or more selected from amino acid sequences as shown in SEQ ID NO: 2, SEQ ID NO: 4, SEQ ID NO: 6 and SEQ ID NO: 38-48.

In another aspect, the present invention provides a nucleotide sequence encoding the above fusion protein.

Preferably, the nucleotide sequence is one or more selected from nucleotide sequences as shown in SEQ ID NO: 1, SEQ ID NO: 3, SEQ ID NO: 5 and SEQ ID NO: 49-59.

Preferably, the nucleotide sequence encoding the transcription control domain is shown in SEQ ID NO: 9.

In further another aspect, the present invention provides a vector for expressing the above fusion protein. Preferably, the vector is retroviral vector. More preferably, the retroviral packaging cell is 293T cell.

The present invention further provides a composition, the composition comprising the above fusion protein, nucleotide sequence and/or expression vector. Preferably, the composition of the present invention further comprises a carrier and an excipient.

Preferably, the composition comprises at least one fusion protein selected from the following group: OCT4-YAP$^{TAD}$ (Oy), SOX2-YAP$^{TAD}$ (Sy), NANOG-YAP$^{TAD}$ (Ny).

Preferably, the composition further comprises Klf4 protein, a nucleotide and/or expression vector encoding Klf4 protein.

Preferably, the expression vector of Klf4 protein is a retroviral vector, more preferably, the retroviral packaging cell is 293T cell.

More preferably, the Klf4 protein has an amino acid sequence as shown in SEQ ID NO: 8.

More preferably, the nucleotide sequence encoding Klf4 protein is shown in SEQ ID NO: 7.

In a preferable embodiment, the composition of the present invention comprises an amino acid sequence as shown in SEQ ID NO: 2, SEQ ID NO: 4, SEQ ID NO: 6 or SEQ ID NO: 8, and/or a nucleotide sequence as shown in SEQ ID NO: 1, SEQ ID NO: 3, SEQ ID NO: 5 and SEQ ID NO: 7.

By using the OCT4-YAP$^{TAD}$, SOX2-YAP$^{TAD}$, NANOG-YAP$^{TAD}$ of the present invention together with KLF4 factor (hereinafter cited as OySyNyK-iPS method), pluripotent stem cells can be induced more efficiently than conventional combination of OCT4, SOX2, NANOG, KLF4 factors (hereinafter cited as OSNK-iPS method).

The present invention further provides a method for reprogramming somatic cells into induced pluripotent stem cells, the method comprising the following steps:

1) treating the somatic cells with the fusion protein, nucleotide sequence, expression vector or composition of the present invention;

2) after culturing, screening out cells with physical and chemical features of pluripotent stem cells, thereby obtaining pluripotent stem cells.

Preferably, the somatic cells are any somatic cells of human or other species. Preferably, the somatic cells are adult somatic cells of a mammal. Further preferably, the mammal is human or mouse. Preferably, the adult somatic cells are: skin fibroblasts, blood cells and/or oral epithelial cells.

Preferably, the method for treating somatic cells comprises introducing the fusion protein, nucleotide, expression vector and/or composition into the somatic cells via viral infection, plasmid transfection, protein transduction and/or mRNA transfection. In a preferable embodiment, the method comprises retroviral infection, preferable, the retroviral packaging cells are 293T cells.

Preferably, in the viral infection, retroviruses in a viral load with multiplicity of infection (MOI) greater than or equal to 10 are used to infect cells. More preferably, retroviruses in a viral load with multiplicity of infection (MOI) equal to 10 are used to infect cells.

In a preferable embodiment of the present invention, step 1) of the method comprises the following steps:

1) constructing a plasmid vector of nucleotide sequence comprising the cell totipotency-related gene of the present invention and the transcriptional activation domain (TAD) of mammal YAP protein or fragment thereof having transcriptional control activity; preferably, further constructing a plasmid vector comprising nucleotide sequence of Klf4; preferably, the nucleotide sequence comprises full-length sequence of OCT4, SOX2, NANOG, the transcriptional activation domain of YAP protein is a transcriptional activation domain (TAD) of mouse YAP protein; preferably, the plasmid is retroviral pMXs vector; preferably, the pMXs vector has a nucleotide sequence as shown in SEQ ID NO: 11;

2) transfecting the above plasmids separately into 293T cells to perform packaging of retroviruses, collecting viral supernatant after transfection for 48 h, then filtering, combining viruses; adding with polybrene, infecting somatic cells, starting cell reprogramming.

Preferably, the filtering uses 0.45 μm PVDF filter.

Preferable, the viruses are mixed in a ratio of 1:1:1:1.

Preferably, the added polybrene has a final concentration of 8 μg/μl.

In an embodiment of the present invention, the used somatic cells are OG2-MEF; after transfection for 24 h, if the removal of viral solution from OG2-MEF cells is recorded as the 0th hour, the soonest expression of Oct4-GFP can be observed at the 20$^{th}$ hour, which suggests the expression of endogenous Oct4 gene starts, and reprogramming has been rapidly launched. The results of cell counting show that the rate of cell proliferation has no significant change, the RT-PCR results show that the expression level of p53 does not change significantly as well. It can be seen that iPS clone starts on about the 4$^{th}$ day, and monoclones with better morphology can be selected for line establishment and culturing on about the 6$^{th}$ to 7$^{th}$ day.

The present invention further provides a kit, the kit comprises the fusion protein, nucleotide sequence, expression vector and/or composition of the present invention.

The present invention further provides a use of the fusion protein, nucleotide sequence, expression vector and/or composition of the present invention in manufacture of a reagent for reprogramming somatic cells into induced stem cells.

The present invention further provides a use of the fusion protein, nucleotide sequence, expression vector and/or composition of the present invention in research and clinical application of regenerative medicine.

In comparison with conventional Oct4, Sox2, Klf4, c-Myc (hereinafter cited as OSMK), the method of the present invention does not use c-Myc, thereby having an improved safety. In comparison with conventional Oct4, Sox2, Nanog, Klf4 (hereinafter cited as OSNK), its induction speed is significantly accelerated, and its induction efficiency is significantly elevated. The results of GFP fluorescence clone counting show that OSNK had nearly no formation of clone on the 7$^{th}$ day, while the iPS induction using OCT4-YAPTAD (Oy), SOX2-YAPTAD (Sy), NANOG-YAPTAD (Ny) and Klf4 (i.e., the OySyNyK method of the present invention) fusion protein combination can form about 2500 fluorescence clones. The results of flow cytometer show that about 40% of cells are Oct4-GFP positive expression cells on the 7th day.

The results of real-time PCR analysis on samples of different time points during iPS induction procedure also show that, for endogenous pluripotency-related genes such as Oct4, Sox2, Nanog, Dax1, Eras and so on, the OySyNyK method can perform induction and expression at a rapid and high level in comparison with the convention OSNK induction. The analysis of cytosine methylation state performed in promoter region of Oct4, Nanog using bisulfite also shows that, in comparison with the convention OSNK induction method, the OySyNyK method can bring about rapid demethylation in promoter regions of Oct4, Nanog within a time period as shorter as 1-2 days, and change them from expression inhibitory state into high-level expression active state. The iPS cell lines after line establishment and passage are same as the iPS cell lines successfully induced and line established by convention Oct4, Sox2, Nanog, Klf4 method, and featured with high-expression of pluripotency-related genes, silent exogenous genes, positive AP staining, ability of inducing and producing EB, generating chimeric mice after blastula injection, and performing germline transmission, which confirm that although they are rapidly and successfully induced, they have good safety as well.

The beneficial effects of the present invention lie in the following two aspects: in comparison with the conventional inefficient and time-consuming pluripotent stem cell induction method, the present invention can form high-quality iPS clones with a very high efficiency within 6-7 days. The subsequent identifications show that the iPS cells produced by this method are very similar to embryonic stem cells in terms of gene expression, proliferation rate and development pluripotency, and can successfully perform germline transmission. Thus, it can be expected that the method can be applied to clinical practices of human regenerative medicine to induce patient-specific auto-pluripotent stem cells rapidly and efficiently, to reduce therapeutic time and increase therapeutic success rate significantly, and to establish a basis for wide application of regenerative medicine in clinic. The present invention can efficiently and rapidly induce the generation of pluripotent stem cells, extremely facilitate research of iPS mechanism, and uncover useful information that is covered by previous low iPS induction efficiency.

The present invention is mainly used for inducing and generating pluripotent stem cells from adult somatic cells, and using them in research of generative medicine and clinical therapy.

In comparison with the conventional inefficient and time-consuming pluripotent stem cell induction method, the present invention can form high-quality iPS clones with a very high efficiency within 6-7 days. The subsequent identifications show that the iPS cells produced by this method are very similar to embryonic stem cells in terms of gene expression, proliferation rate and development pluripotency, and can successfully perform germline transmission. Thus, it can be expected that the method can be applied to clinical practices of human regenerative medicine to induce patient-specific auto-pluripotent stem cells rapidly and efficiently, to reduce therapeutic time and increase therapeutic success rate significantly, and to establish a basis for wide application of regenerative medicine in clinic.

BRIEF DESCRIPTION OF THE DRAWINGS

Hereinafter, the embodiments of the present invention are illustrated in conjunction with drawings, wherein.

DETAILED DESCRIPTION OF THE INVENTION

Figure 1:
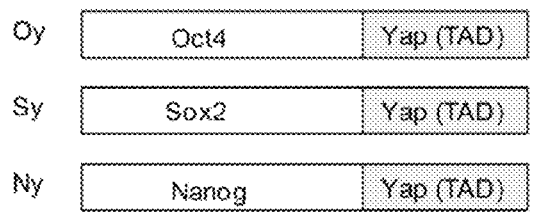
FIG. 1 shows a schematic diagram for constructing Oct4-YAP$^{TAD}$, SOX2-YAP$^{TAD}$, NANOG-YAP$^{TAD}$ vectors of the present invention.
Figure 2:
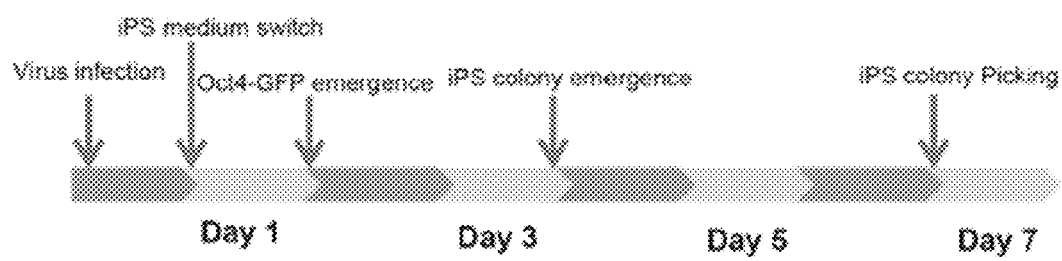
FIG. 2 shows a schematic diagram of time of forming pluripotent stem cells by induction of the OySyNyK method.
Figure 3:
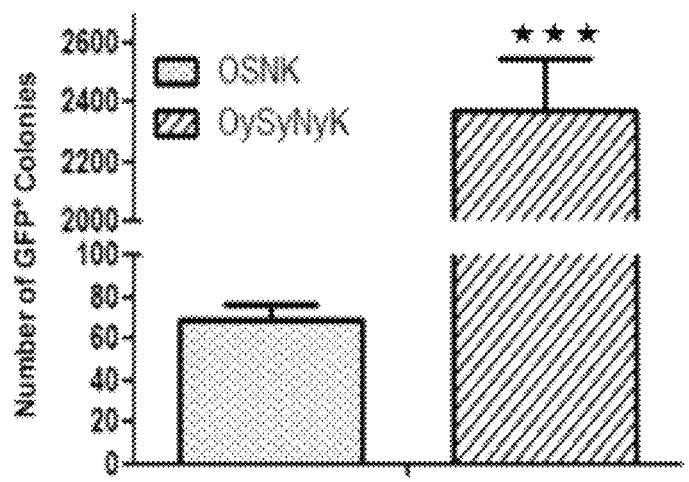
FIG. 3 shows results of GFP positive clone counting, and comparison of efficiency of inducing iPS by OySyNyK method and efficiency of inducing iPS by OSNK method, wherein, the counting was carried out on the 12$^{th}$ day for OSNK method, while the counting was carried out on the 7$^{th}$ day for OySyNyk method.
Figure 4:
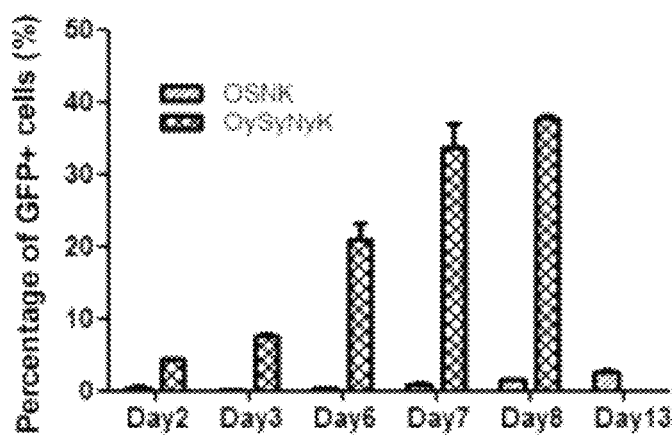
FIG. 4 shows proportions of GFP positive cells analyzed by flow cytometer, and the results show that OySyNyK induction method is more rapid and efficient than the OSNK induction method.

The present invention is illustrated as follows by referring to specific examples. Those skilled in the art would understand that these examples are merely used for illustrating the present invention, rather than restricting the protection scope of the present invention in any way.

Unless specifically pointing out, all reagents used in the following examples are of analytically pure grade, and commercially available.

Embodiment 1: Induction of Pluripotent Stem Cells by Using OySyNyK Method 1.1 Main Reagents and Materials HEK293T culture media formula: high-glucose DMEM culture media, which was added with 10% fetal bovine serum as well as penicillin 100 U/ml and streptomycin 100 μg/ml in final concentrations.

MEF culture media formula: high-glucose DMEM culture media, which was added with 10% fetal bovine serum, 0.055 mM β-mercaptoethanol, 2 mM L-glutamine, 0.1 mM non-essential amino acids, as well as penicillin 100 U/ml and streptomycin 100 μg/ml in final concentrations.

iPSC culture media formula: high-glucose DMEM culture media, which was added with 10% fetal bovine serum, 0.055 mM β-mercaptoethanol, 2 mM L-glutamine, 0.1 mM non-essential amino acids, as well as penicillin 100 U/ml, streptomycin 100 μg/ml, 50 μg/ml vitamin C (Sigma), and LIF 1000 U/ml in final concentrations.

1.2 Experimental Methods

Retroviruses were prepared by a conventional method known in the art, in which pMXs retroviral vector (purchased from Addgene) plasmids were separately Oct4-Yap$^{TAD}$(Oy), Sox2-Yap$^{TAD}$ (Sy), Nanog-Yap$^{TAD}$ (Ny), Klf4 (K) and packaging plasmid, each in amount of 11 were used to transfect HEK293T cells by calcium phosphate precipitation method. After transfection for 12 h, fresh culture media was used for replacement. After transfection for 48 h, viral supernatant was collected, and filtered with 0.45 μm PVDF filter. OCT4-GFP MEF (primary passage embryo fibroblasts as prepared from OCT4-GFP transgenic mice (purchased from Jackson Laboratory) with pregnancy for 13.5 days) was inoculated 16 h ahead in density of 5×10$^4$ on a 12-well plate. The 4 kinds of viruses were mixed in a ratio of 1:1:1:1, and added with polybrene in final concentration of 8 μg/ml, and infection was carried out by using a viral load of 2 ml per well. After infection for 24 h, iPS culture media were used for replacement, and this time was defined as the 0$^{th}$ hour. After about 24±6 hr, expression of single cell OCT4-GFP started, and OCT4-GFP positive iPSC clone started to appear on the 3$^{rd}$ day. The counting of iPSC was carried out or the monoclones were selected for passage on the 6$^{th}$ or 7$^{th}$ day.

Embodiment 2: Induction of Pluripotent Stem Cells by Using OSNK Method

HEK293T culture media formula: high-glucose DMEM culture media, which was added with 10% fetal bovine serum as well as penicillin 100 U/ml and streptomycin 100 μg/ml in final concentrations.

MEF culture media formula: high-glucose DMEM culture media, which was added with 10% fetal bovine serum, 0.055 mM β-mercaptoethanol, 2 mM L-glutamine, 0.1 mM non-essential amino acids, as well as penicillin 100 U/ml and streptomycin 100 μg/ml in final concentrations.

iPSC culture media formula: high-glucose DMEM culture media, which was added with 10% fetal bovine serum, 0.055 mM β-mercaptoethanol, 2 mM L-glutamine, 0.1 mM non-essential amino acids, as well as penicillin 100 U/ml, streptomycin 100 μg/ml, 50 μg/ml vitamin C (Sigma), and LIF 1000 U/ml in final concentrations.

Retrovirus packaging: pMXs retroviral vector (purchased from Addgene) plasmids (which were separately Oct4 (O), Sox2 (S), Nanog (N), Klf4(K)), and Ecopac packaging plasmid, each in amount of 11 μg, were used to transfect HEK293T cells by calcium phosphate precipitation method. After transfection for 12 h, fresh culture media was used for replacement. After transfection for 48 h, viral supernatant was collected, and filtered with 0.45 μm PVDF filter. OCT4-GFP MEF was inoculated 16 h in advance in density of 5×10$^4$ on a 12-well plate. The 4 kinds of viruses were mixed in a ratio of 1:1:1:1, and added with polybrene in final concentration of 8 μg/ml, and infection was carried out by using a viral load of 2 ml per well. After infection for 24 h, iPS culture media were used for replacement, and this time was defined as the 0$^{th}$ hour. The expression of OCT4-GFP was observed on about the 4$^{th}$ day, OCT4-GFP positive iPSC clone started to appear on the 7$^{th}$ day, and the counting of iPS clones was carried out or monoclones were selected for passage between the 12$^{th}$ and 14$^{th}$ day.

Embodiment 3: Morphological Structures and GFP Expression Identification of the Induced Pluripotent Stem Cells of the OySyNyK Method and the OSNK Method GFP reporter plasmids in which OCT4-GFP was driven to express by Oct4 promoter were integrated into genome of transgenic mice, which were used to indicate endogenous Oct4 gene expression and were an important index for iPS pluripotency.

Figure 5:
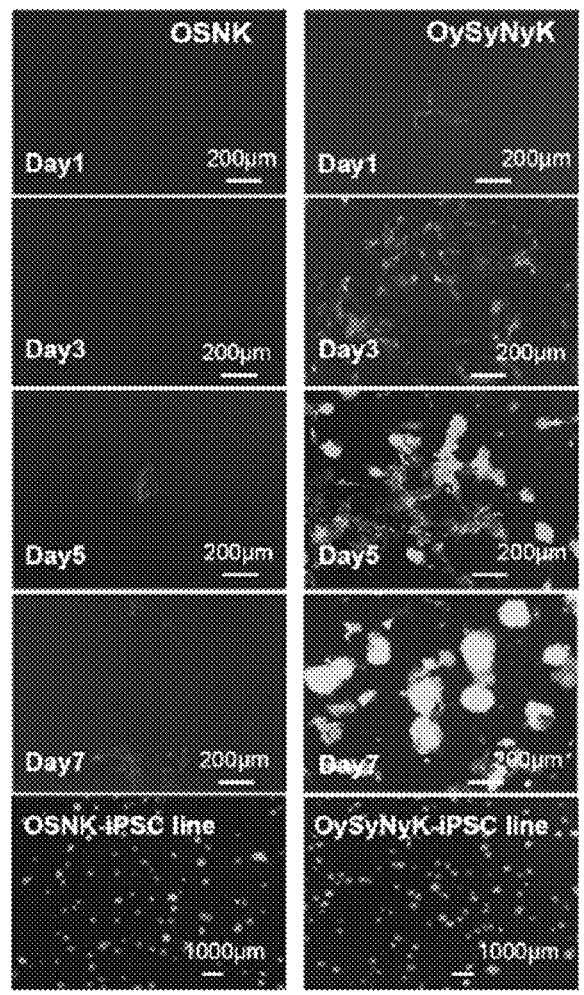
FIG. 5 shows GFP fluorescence pictures, which are used for comparison of different speeds and efficiencies of iPS induction by the conventional OSNK method and iPS induction by the OySyNyK method of the present invention.

As shown in FIG. 5, the conventional OSNK induced pluripotent stem cells shows low efficiency and long time-consuming, in which a small amount OCT4-GFP cell expression started on about the 5$^{th}$ day, and obvious iPS clones were not observed on the 7$^{th}$ day. On the contrary, in the method of the present invention, OCT4-GFP expression appeared on the 1$^{st}$ day, primary formation of iPS clones started on the 3$^{rd}$ day, and a large amount of iPS clones in good state were formed on the 7$^{th}$ day. After line establishment and passages, the iPS clones formed by the method of the present invention showed no significant morphological difference in comparison with the iPS clones produced by induction of the conventional OSNK method.

Embodiment 4: Alkaline Phosphatase Staining Identification of Induced Pluripotent Stem Cells of the OySyNyK Method and the OSNK Method Alkaline phosphatase staining was performed by using kits of Millipore, and has specific steps as follows:

Cell culture solution was drawn off, moistened and washed with PBS once, fixed with PFA for 1-2 min. Fixing solution was drawn off, TBST was used for moistening and washing once. To each well of 12-well plate, 1 ml of alkaline phosphatase reagent was added, after 10-15 min of standing away from light at room temperature, staining solution was drawn off, PBS buffer solution was used for moistening and washing once, and the cells were finally stored in PBS solution.

Figure 6:
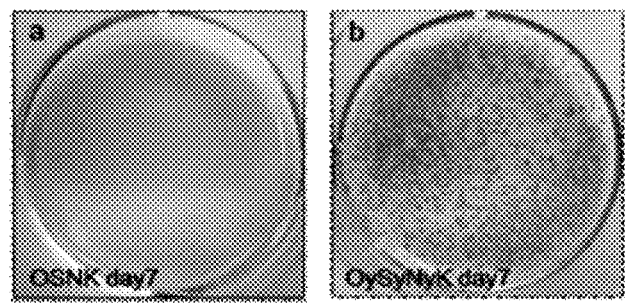
FIG. 6 shows results of alkaline phosphatase staining (NAP), and the results indicate that on the 7$^{th}$ day the OySyNyK method shows very high efficiency in iPS induction, while the OSNK method induces the generation of few iPS clones.

As shown in FIG. 6, on the 7$^{th}$ day, the iPS induced by the OSNK method showed no significant staining, while the iPS induced by the method of the present invention showed a large amount of alkaline phosphatase staining positive clones.

Figure 7:
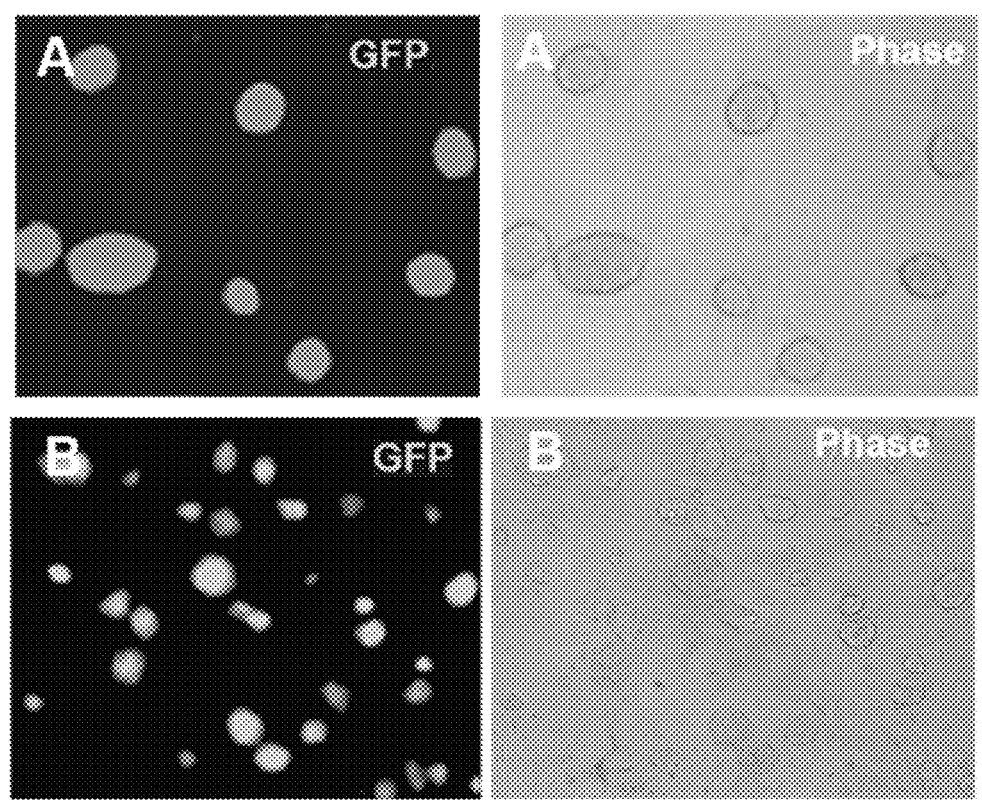
FIG. 7 shows that the clones formed by induction of the OySyNyK method have a morphology after line establishment and passage similar to morphology of mES, and good state can be maintained after long-term of passage. Figure A shows the morphology of iPS clone of the 1$^{st}$ passage after line establishment, and Figure B shows the morphology of iPS clone of the 10$^{th}$ passage after line establishment.

Embodiment 5: Typical Pluripotent Stem Cell Growth Characteristics of Most of the iPS Generated by Induction of the OySyNyK Method FIG. 7 showed that after line establishment and passages, the iPS clones generated by induction of the OySyNyK method could well maintain clonal morphology similar to that of embryonic stem cells, and typical clonal morphology was still maintained after long-term of culture (consecutive 10 passages).

Embodiment 6: Expression Identification of mRNA Levels of the Induced Pluripotent Stem Cells of the OySyNyK Method and the OSNK Method In the procedures for induction of iPS by the OSNK method and the OySyNyK method, cells were collected on the designated days, and lysed by Trizol, then RNA was extracted. 2 μg of RNA was taken to perform inverse transcription to generate cDNA, then real-time PCR analysis was performed.

Primer sequences are as follows:

OCT4:
(SEQ ID NO: 12)
Forward direction:  5'-TAGGTGAGCCGTCTTTCCAC-3'

```
                                           (SEQ ID NO: 13)
Reverse direction:   5'-GCTTAGCCAGGTTCGAGGAT-3'

SOX2:
                                           (SEQ ID NO: 14)
Forward direction:   5'-AGGGCTGGGAGAAAGAAGAG-3'

(SEQ ID NO: 15)
Reverse direction:   5'-CCGCGATTGTTGTGATTAGT-3'

NANOG2:
                                           (SEQ ID NO: 16)
Forward direction:   5'-ATCCCTTCCCTCGCCATCAC-3'

(SEQ ID NO: 17)
Reverse direction:   5'-GGCATTGATGAGGCGTTCC-3'

Dax1
                                           (SEQ ID NO: 18)
Forward direction:   5'-TGCTGCGGTCCAGGCCATCAAGAG-3'

(SEQ ID NO: 19)
Reverse direction:   5'-GGGCACTGTTCAGTTCAGCGGATC-3'

Eras
                                           (SEQ ID NO: 20)
Forward direction:   5'-TGCCTACAAAGTCTAGCATCTTG-3'

(SEQ ID NO: 21)
Reverse direction:   5'-CTTTTACCAACACCACTTGCAC-3'

GAPDH:
                                           (SEQ ID NO: 22)
Forward direction:   5'-AGTCAAGGCCGAGAATGGGAAG-3'

(SEQ ID NO: 23)
Reverse direction:   5'-AAGCAGTTGGTGGTGCAGGATG-3'
```

Figure 8:
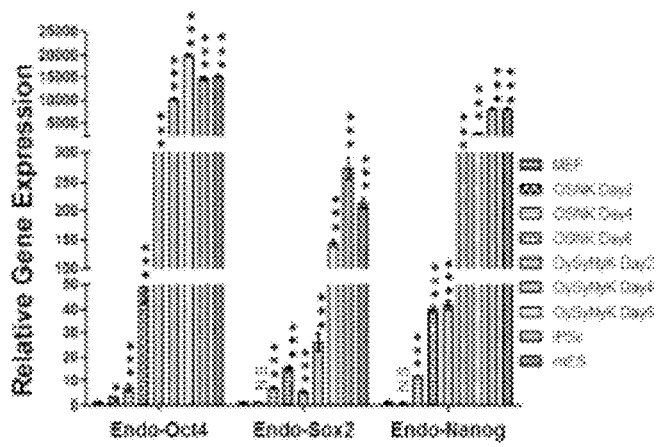
FIG. 8 shows expression identification of mRNA level of induced pluripotent stem cells, and as shown in the figure, the OySyNyK method can more rapidly and more efficiently induce the expression of endogenous pluripotent factors OCT4, SOX2, NANOG than the OSNK method.
Figure 9:
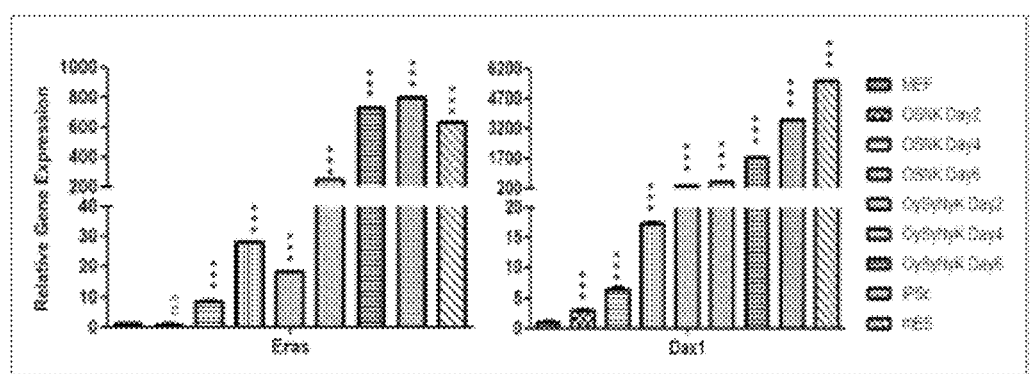
FIG. 9 shows expression identification of mRNA level of induced pluripotent stem cells, and as shown in the figure, the OySyNyK method can more rapidly and more efficiently induce the expression of endogenous pluripotent factors Eras, Dax1 than the OSNK method.

As shown in FIG. 8, in comparison with the OSNK method, the OySyNyK method could more rapidly and efficiently induce the expression of endogenous pluripotent factors OCT4, SOX2, NANOG; as shown in FIG. 9, in comparison with the OSNK method, the OySyNyK method could more rapidly and efficiently induce the expression of endogenous pluripotent factors Eras, Dax1.

Embodiment 7: Tests of In Vitro Formation of Teratoma

Figure 12:
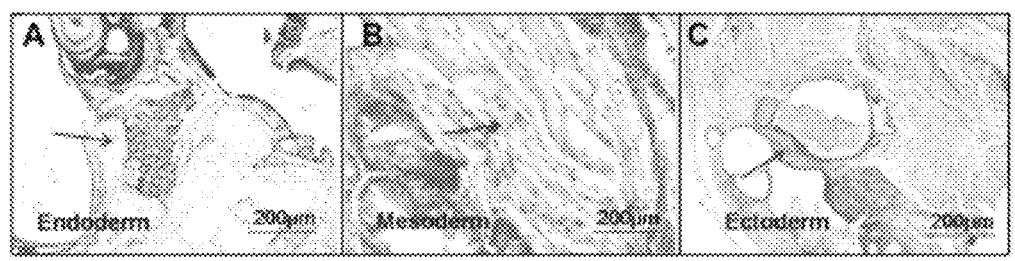
FIG. 12 shows the generation of teratoma on immunodeficient mice injected with OySyNyK-iPSc of the present invention, in which HE stain exhibits structure of 3 blastoderms.
Figure 13:
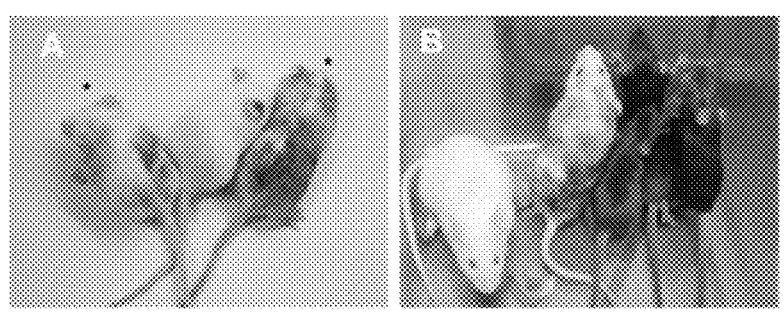
FIG. 13 shows the generation of chimeric mice (FIG. A) by blastula injection of OySyNyK-iPSc of the present invention, and the generation of germline transmission mice (FIG. B).

After feeder was removed from iPS cells of induction and line establishment by the OySyNyK method, the cells in amount of 2*10$^6$ were injected to SCID naked mice (purchased from Vital River) at upper part of hind leg, teratoma tissues were collected after about 2 months and subjected to hematoxylin and eosin staining. As shown in FIG. 12, the teratoma generated by the iPS of induction and line establishment by the OySyNyK method had structure of 3 blastoderms, which confirmed the totipotency of the iPS cell line.

Embodiment 8: Silence of Retrovirus Exogenous Gene Expression

The samples of 6 iPS cell lines obtained by induction of the OySyNyK method and line establishment and passage were taken on the 3$^{rd}$ day after the OySyNyK viruses infected MEF, the MEF cells were subjected to Trizol lysis, RNA was extracted, 2 μg of RNA was subjected to inverse transcription to generate cDNA, then real-time PCR analysis was performed. The primer sequences were as follows:

```
OCT4:
                                           (SEQ ID NO: 24)
Forward direction:   5'-GGGTGGACCATCCTCTAGAC-3'

(SEQ ID NO: 25)
Reverse direction:   5'-CCAGGTTCGAGAATCCAC-3'

SOX2:
                                           (SEQ ID NO: 26)
Forward direction:   5'-GGGTGGACCATCCTCTAGAC-3'

(SEQ ID NO: 27)
Reverse direction:   5'-GGGCTGTTCTTCTGGTTG-3'

NANOG:
                                           (SEQ ID NO: 28)
Forward direction:   5'-GGGTGGACCATCCTCTAGAC-3'

(SEQ ID NO: 29)
Reverse direction:   5'-GGCATTGATGAGGCGTTCC-3'

KLF4:
                                           (SEQ ID NO: 30)
Forward direction:   5'-GGGTGGACCATCCTCTAGAC-3'

(SEQ ID NO: 31)
Reverse direction:   5'-GCTGGACGCAGTGTCTTCTC-3'

GAPDH:
                                           (SEQ ID NO: 32)
Forward direction:   5'-AGTCAAGGCCGAGAATGGGAAG-3'

(SEQ ID NO: 33)
Reverse direction:   5'-AAGCAGTTGGTGGTGCAGGATG-3'
```

Figure 10:
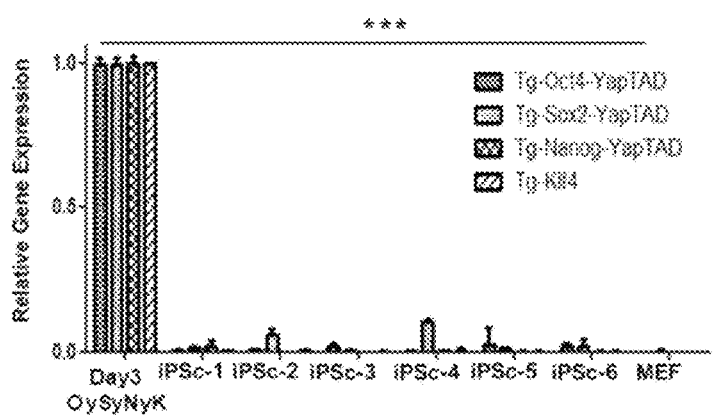
FIG. 10 shows using the iPSc successfully induced by the OySyNyK method of the present invention to line establishment and passage, and in the 6 cell lines for line establishment as shown in the figure, exogenously expressed inducing genes are all silent.
Figure 11:
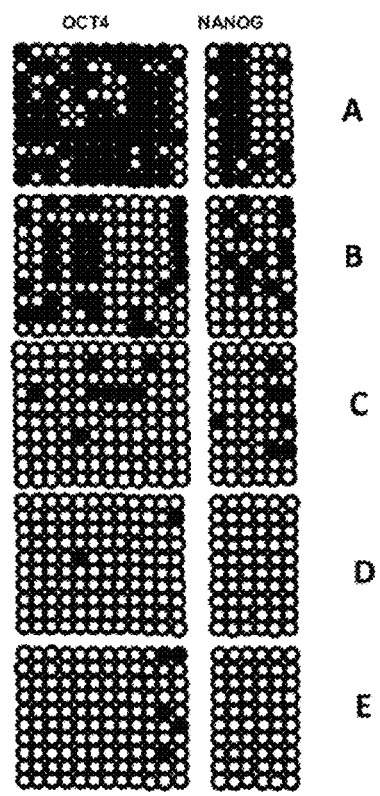
FIG. 11 shows the iPS induction carried out by the OySyNyK method of the present invention, in which bisulfite sequencing method can be used to detect the promoter regions of Oct4, Nanog cell factors change on the 3$^{rd}$ day from epigenetic inhibition state into activity expression state; FIG. A shows MEF sample; FIG. B shows FACS screened GFP positive cells of the 3$^{rd}$ day sample of iPS induction by OySyNyK method; FIG. C shows FACS screened GFP positive cells of the 5$^{th}$ day sample of iPS induction by OySyNyK method; FIG. D shows line establishment cell sample of iPS induction by OySyNyK method; and FIG. F shows mES positive control sample.

As shown in FIG. 10, in the 6 iPS cell lines obtained by induction of the OySyNyK method and line establishment and passage, all exogenously expressed Oy, Sy, Ny, K were of expression silencing state.

Embodiment 9: Rapid Demethylation of Oct4 and Nanog Promoters During iPS Induction of the OySyNyK Method Genomes of various samples were extracted, then treated with bisulfite. This test used the CpGenome™ Turbo Bisulfite Modification Kit of Millipore for treatment of samples. The products were subjected to PCR of Oct4 and Nanog promoter regions, the PCR products were subjected to blunt-end ligation with pEASY-T3 vector (purchased from Transgen), 10 clones were randomly selected for sequencing. The primer information was as follows:

```
DNA methylation analysis of NANOG promoter
Forward direction:
                                           (SEQ ID NO: 34)
5'-GATTTTGTAGGTGGGATTAATTGTGAATTT-3'

Reverse direction:
                                           (SEQ ID NO: 35)
5'-ACCAAAAAAACCCACACTCATATCAATATA-3'

DNA methylation analysis of OCT4 promoter:
Forward direction:
                                           (SEQ ID NO: 36)
5'-ATGGGTTGAAATATTGGGTTTATTTA-3'

Reverse direction:
                                           (SEQ ID NO: 37)
5'-CCACCCTCTAACCTTAACCTCTAAC-3'
```

The analysis of cytosine methylation states of Oct4, Nanog promoter regions showed that, in comparison with the conventional OSNK induction method, the OySyNyK method could bring about rapid demethylation in promoter regions of Oct4, Nanog within a time period as shorter as 1-2 days, and change them from expression inhibitory state into high-level expression active state.

Embodiment 10: Use of the iPS Induced by OySyNyK Method in Generation of Chimeric Mice and Germline Transmission The iPS induced by the OySyNyK method was injected into 3.5 days blastulas of ICR mice, then blastulas were transplanted into uteruses of surrogacy female mice. In the produced off-spring mice, there were chimeric mice with mixed coat colors, then the chimeric male mice were mated with wild-type ICR female mice, and there were pure black mice among the produced off-spring mice.

As shown in left side of the figure, the iPS induced by the OySyNyK method could successfully produce chimeric mice. As shown in right side of the figure, the produced chimeric mice could successfully perform germline transmission. These indicate that the iPS induced by the OySyNyK method had good pluripotency.

What is claimed is:

1. A method for reprogramming somatic cells into induced pluripotent stem cells, the method comprising the following steps:

providing an OCT4-YAP$^{TAD}$ plasmid, a SOX2-YAP$^{TAD}$ plasmid, a NANOG-YAP$^{TAD}$ plasmid, a Klf4 plasmid, and a packaging plasmid, wherein the OCT4-YAP$^{TAD}$ plasmid comprises a nucleotide sequence set forth in SEQ ID NO:1, the SOX2-YAP$^{TAD}$ plasmid comprises a nucleotide sequence set forth in SEQ ID NO:3, the NANOG-YAP$^{TAD}$ plasmid comprises a nucleotide sequence set forth in SEQ ID NO:5, and the Klf4 plasmid comprises a nucleotide sequence set forth in SEQ ID NO:7;

transfecting 293T cells respectively with the OCT4-YAP$^{TAD}$ plasmid, the SOX2-YAP$^{TAD}$ plasmid, the NANOG-YAP$^{TAD}$ plasmid, the Klf4 plasmid, and the packaging plasmid to obtain viruses, wherein the viruses respectively contain the nucleotide sequence set forth in SEQ ID NO:1, the nucleotide sequence set forth in SEQ ID NO:3, the nucleotide sequence set forth in SEQ ID NO:5, and the nucleotide sequence set forth in SEQ ID NO:7;

transfecting the somatic cells with the viruses;

culturing the transfected somatic cells; and screening the cultured somatic cells to obtain the induced pluripotent stem cells.

2. The method according to claim 1, wherein the OCT4-YAP$^{TAD}$ plasmid, the SOX2-YAP$^{TAD}$ plasmid, the NANOG-YAP$^{TAD}$ plasmid, and the Klf4 plasmid are constructed using a pMXs vector, and the pMXs vector has a nucleotide sequence set forth in SEQ ID NO:11.

3. The method according to claim 1, wherein the somatic cells comprise skin fibroblasts, blood cells and oral epithelial cells.

4. A method for reprogramming somatic cells into induced pluripotent stem cells, the method comprising the following steps:

providing an OCT4-YAP$^{TAD}$ fusion protein, a SOX2-YAP$^{TAD}$ fusion protein, a NANOG-YAP$^{TAD}$ fusion protein, and a Klf4 protein, wherein the OCT4-YAP$^{TAD}$ fusion protein comprises an amino acid sequence set forth in SEQ ID NO:2, the SOX2-YAP$^{TAD}$ fusion protein comprises an amino acid sequence set forth in SEQ ID NO:4, the NANOG-YAP$^{TAD}$ fusion protein comprises an amino acid sequence set forth in SEQ ID NO:6, and the Klf4 protein comprises an amino acid sequence set forth in SEQ ID NO:8;

treating the somatic cells with the OCT4-YAP$^{TAD}$ fusion protein, the SOX2-YAP$^{TAD}$ fusion protein, the NANOG-YAP$^{TAD}$ fusion protein, and the Klf4 protein;

culturing the treated somatic cells; and screening the cultured somatic cells to obtain the induced pluripotent stem cells.

* * * * *

SEQUENCE LISTING

```
<160> NUMBER OF SEQ ID NOS: 59

<210> SEQ ID NO 1
<211> LENGTH: 1707
<212> TYPE: DNA
<213> ORGANISM: Artificial Sequence
<220> FEATURE:
<223> OTHER INFORMATION: Nucleotide sequence encoding fusion protein of
      OCT4 and transactivation domain of YAP

<400> SEQUENCE: 1
atggctggac acctggcttc agacttcgcc ttctcacccc caccaggtgg gggtgatggg      60
tcagcagggc tggagccggg ctgggtggat tctcgaacct ggctaagctt ccaagggcct     120
ccaggtgggc ctggaatcgg accaggctca gaggtattgg ggatctcccc atgtccgccc     180
gcatacgagt tctgcggagg gatggcatac tgtggacctc aggttggact gggcctagtc     240
ccccaagttg gcgtggagac tttgcagcct gagggccagg caggagcacg agtggaaagc     300
aactcagagg gaacctcctc tgagccctgt gccgaccgcc caatgccgt gaagttggag      360 aaggtggaac caactcccga ggagtcccag gacatgaaag ccctgcagaa ggagctagaa     420
cagtttgcca agctgctgaa gcagaagagg atcaccttgg ggtacaccca ggccgacgtg     480
gggctcaccc tgggcgttct ctttggaaag gtgttcagcc agaccaccat ctgtcgcttc     540
gaggccttgc agctcagcct taagaacatg tgtaagctgc ggcccctgct ggagaagtgg     600
gtggaggaag ccgacaacaa tgagaaccct caggagatat gcaaatcgga gaccctggtg     660
caggcccgga gagaaagcg aactagcatt gagaaccgtg tgaggtggag tctggagacc     720
atgtttctga gtgcccgaa gccctcccta cagcagatca ctcacatcgc caatcagctt     780
gggctagaga aggatgtggt tcgagtatgg ttctgtaacc ggcgccagaa gggcaaaaga     840
tcaagtattg agtattccca acgagaagag tatgaggcta cagggacacc tttcccaggg     900
ggggctgtat cctttcctct gccccaggt cccactttg gcacccagg ctatggaagc        960 ccccacttca ccacactcta ctcagtccct tttcctgagg gcgaggcctt tccctctgtt    1020
cccgtcactg ctctgggctc tcccatgcat tcaaacgcgg ccgcacaggg aggcgtcctg    1080
ggtggaggca gttccaacca gcagcagcaa atacagctgc agcagttaca gatggagaag    1140
gagagactgc ggttgaaaca acaggaatta tttggcagg caatacggaa tatcaatccc     1200
agcacagcaa atgctccaaa atgtcaggaa ttagctctgc gcagccagtt gcctacactg    1260
gagcaggatg gagggactcc gaatgcagtg tcttctcctg ggatgtctca ggaattgaga    1320
acaatgacaa ccaatagttc cgatcccttt cttaacagtg gcacctatca ctctcgagat    1380
gagagcacag acagcggcct cagcatgagc agctacagca tccctcggac cccagacgac    1440
ttcctcaaca gtgtggatga atggatata ggagacacca tcagccaaag caccctgccg     1500
tcacagcaga gccgcttccc cgactacctg gaagccctcc ctgggacaaa tgtggacctt    1560
ggcacactgg aaggagatgc aatgaacata gaaggggagg agctgatgcc cagtctgcag    1620
gaagcgctga gttccgaaat cttggacgtg gagtctgtgt tggctgccac caagctagat   1680
```
aaagaaagct ttctcacgtg gttatag        1707

<210> SEQ ID NO 2
<211> LENGTH: 568
<212> TYPE: PRT
<213> ORGANISM: Artificial Sequence
<220> FEATURE:
<223> OTHER INFORMATION: Fusion protein of OCT4 and transactivation
      domain of YAP

<400> SEQUENCE: 2

```
Met Ala Gly His Leu Ala Ser Asp Phe Ala Phe Ser Pro Pro Pro Gly
1               5                   10                  15

Gly Gly Asp Gly Ser Ala Gly Leu Glu Pro Gly Trp Val Asp Ser Arg
            20                  25                  30

Thr Trp Leu Ser Phe Gln Gly Pro Pro Gly Gly Pro Gly Ile Gly Pro
        35                  40                  45

Gly Ser Glu Val Leu Gly Ile Ser Pro Cys Pro Pro Ala Tyr Glu Phe
    50                  55                  60

Cys Gly Gly Met Ala Tyr Cys Gly Pro Gln Val Gly Leu Gly Leu Val
65                  70                  75                  80

Pro Gln Val Gly Val Glu Thr Leu Gln Pro Glu Gly Gln Ala Gly Ala
                85                  90                  95

Arg Val Glu Ser Asn Ser Glu Gly Thr Ser Ser Glu Pro Cys Ala Asp
            100                 105                 110

Arg Pro Asn Ala Val Lys Leu Glu Lys Val Glu Pro Thr Pro Glu Glu
        115                 120                 125

Ser Gln Asp Met Lys Ala Leu Gln Lys Glu Leu Glu Gln Phe Ala Lys
    130                 135                 140

Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                165                 170                 175

Ile Cys Arg Phe Glu Ala Leu Gln Leu Ser Leu Lys Asn Met Cys Lys
            180                 185                 190

Leu Arg Pro Leu Leu Glu Lys Trp Val Glu Glu Ala Asp Asn Asn Glu
        195                 200                 205

Asn Leu Gln Glu Ile Cys Lys Ser Glu Thr Leu Val Gln Ala Arg Lys
    210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                245                 250                 255

Ala Asn Gln Leu Gly Leu Glu Lys Asp Val Val Arg Val Trp Phe Cys
            260                 265                 270

Asn Arg Arg Gln Lys Gly Lys Arg Ser Ser Ile Glu Tyr Ser Gln Arg
        275                 280                 285

Glu Glu Tyr Glu Ala Thr Gly Thr Pro Phe Pro Gly Gly Ala Val Ser
    290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                325                 330                 335

Phe Pro Ser Val Pro Val Thr Ala Leu Gly Ser Pro Met His Ser Asn
            340                 345                 350
```

Ala Ala Ala Gln Gly Gly Val Leu Gly Gly Gly Ser Ser Asn Gln Gln
        355                 360                 365

Gln Gln Ile Gln Leu Gln Gln Leu Gln Met Glu Lys Glu Arg Leu Arg
    370                 375                 380

Leu Lys Gln Gln Glu Leu Phe Arg Gln Ala Ile Arg Asn Ile Asn Pro
385                 390                 395                 400

Ser Thr Ala Asn Ala Pro Lys Cys Gln Glu Leu Ala Leu Arg Ser Gln
                405                 410                 415

Leu Pro Thr Leu Glu Gln Asp Gly Gly Thr Pro Asn Ala Val Ser Ser
            420                 425                 430

Pro Gly Met Ser Gln Glu Leu Arg Thr Met Thr Thr Asn Ser Ser Asp
        435                 440                 445

Pro Phe Leu Asn Ser Gly Thr Tyr His Ser Arg Asp Glu Ser Thr Asp
    450                 455                 460

Ser Gly Leu Ser Met Ser Ser Tyr Ser Ile Pro Arg Thr Pro Asp Asp
465                 470                 475                 480

Phe Leu Asn Ser Val Asp Glu Met Asp Thr Gly Asp Thr Ile Ser Gln
                485                 490                 495

Ser Thr Leu Pro Ser Gln Gln Ser Arg Phe Pro Asp Tyr Leu Glu Ala
            500                 505                 510

Leu Pro Gly Thr Asn Val Asp Leu Gly Thr Leu Glu Gly Asp Ala Met
        515                 520                 525

Asn Ile Glu Gly Glu Glu Leu Met Pro Ser Leu Gln Glu Ala Leu Ser
    530                 535                 540

Ser Glu Ile Leu Asp Val Glu Ser Val Leu Ala Ala Thr Lys Leu Asp
545                 550                 555                 560

Lys Glu Ser Phe Leu Thr Trp Leu
                565

<210> SEQ ID NO 3
<211> LENGTH: 1608
<212> TYPE: DNA
<213> ORGANISM: Artificial Sequence
<220> FEATURE:
<223> OTHER INFORMATION: Nucleotide sequence encoding fusion protein of
      SOX2 and transactivation domain of YAP

<400> SEQUENCE: 3
atgtataaca tgatggagac ggagctgaag ccgccgggcc cgcagcaagc ttcgggggc     60 ggcggcggag gaggcaacgc cacggcggcg gcgaccggcg gcaaccagaa gaacagcccg    120
gaccgcgtca gaggcccat gaacgccttc atggtatggt cccgggggca gcggcgtaag    180
atggcccagg agaaccccaa gatgcacaac tcggagatca gcaagcgcct gggcgcggag    240
tggaaacttt tgtccgagac cgagaagcgg ccgttcatcg acgaggccaa gcggctgcgc    300
gctctgcaca tgaaggagca cccggattat aaataccggc cgcggcggaa aaccaagacg    360
ctcatgaaga aggataagta cacgcttccc ggaggcttgc tggcccccgg cgggaacagc    420
atggcgagcg gggttggggt gggcgccggc ctgggtgcgg gcgtgaacca gcgcatggac    480
agctacgcgc acatgaacgg ctggagcaac ggcagctaca gcatgatgca ggagcagctg    540
ggctacccgc agcacccggg cctcaacgct cacggcgcgg cacagatgca accgatgcac    600
cgctacgacg tcagcgccct gcagtacaac tccatgacca gctcgcagac ctacatgaac    660
ggctcgccca cctacagcat gtcctactcg cagcagggca cccccggtat ggcgctgggc    720
tccatgggct ctgtggtcaa gtccgaggcc agctccagcc cccccgtggt tacctcttcc    780

```
tcccactcca gggcgccctg ccaggccggg gacctccggg acatgatcag catgtacctc    840
cccggcgccg aggtgccgga gcccgctgcg cccagtagac tgcacatggc ccagcactac    900
cagagcggcc cggtgcccgg cacggccatt aacggcacac tgcccctgtc gcacatggcg    960
gccgcacagg gaggcgtcct gggtggaggc agttccaacc agcagcagca aatacagctg   1020
cagcagttac agatggagaa ggagagactg cggttgaaac aacaggaatt atttcggcag   1080
gcaatacgga atatcaatcc cagcacagca atgctccaa aatgtcagga attagctctg    1140
cgcagccagt tgcctacact ggagcaggat ggagggactc cgaatgcagt gtcttctcct   1200
gggatgtctc aggaattgag aacaatgaca accaatagtt ccgatccctt tcttaacagt   1260
ggcacctatc actctcgaga tgagagcaca gacagcggcc tcagcatgag cagctacagc   1320
atccctcgga ccccagacga cttcctcaac agtgtggatg aaatggatac aggagacacc   1380
atcagccaaa gcaccctgcc gtcacagcag agccgcttcc ccgactacct ggaagccctc   1440
cctgggacaa atgtggacct tggcacactg gaaggagatg caatgaacat agaaggggag   1500
gagctgatgc ccagtctgca ggaagcgctg agttccgaaa tcttggacgt ggagtctgtg   1560
ttggctgcca ccaagctaga taaagaaagc tttctcacgt ggttatag                1608
```

<210> SEQ ID NO 4
<211> LENGTH: 535
<212> TYPE: PRT
<213> ORGANISM: Artificial Sequence
<220> FEATURE:
<223> OTHER INFORMATION: Fusion protein of SOX2 and transactivation domain of YAP

<400> SEQUENCE: 4

```
Met Tyr Asn Met Met Glu Thr Glu Leu Lys Pro Pro Gly Pro Gln Gln
1               5                   10                  15

Ala Ser Gly Gly Gly Gly Gly Gly Asn Ala Thr Ala Ala Ala Thr
            20                  25                  30

Gly Gly Asn Gln Lys Asn Ser Pro Asp Arg Val Lys Arg Pro Met Asn
        35                  40                  45

Ala Phe Met Val Trp Ser Arg Gly Gln Arg Arg Lys Met Ala Gln Glu
    50                  55                  60

Asn Pro Lys Met His Asn Ser Glu Ile Ser Lys Arg Leu Gly Ala Glu
65                  70                  75                  80

Trp Lys Leu Leu Ser Glu Thr Glu Lys Arg Pro Phe Ile Asp Glu Ala
                85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
    130                 135                 140

Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205
```

-continued

Tyr Asn Ser Met Thr Ser Ser Gln Thr Tyr Met Asn Gly Ser Pro Thr
    210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Pro Pro Val
            245                 250                 255

Val Thr Ser Ser Ser His Ser Arg Ala Pro Cys Gln Ala Gly Asp Leu
        260                 265                 270

Arg Asp Met Ile Ser Met Tyr Leu Pro Gly Ala Glu Val Pro Glu Pro
            275                 280                 285

Ala Ala Pro Ser Arg Leu His Met Ala Gln His Tyr Gln Ser Gly Pro
    290                 295                 300

Val Pro Gly Thr Ala Ile Asn Gly Thr Leu Pro Leu Ser His Met Ala
305                 310                 315                 320

Ala Ala Gln Gly Gly Val Leu Gly Gly Ser Ser Asn Gln Gln Gln
            325                 330                 335

Gln Ile Gln Leu Gln Gln Leu Gln Met Glu Lys Glu Arg Leu Arg Leu
            340                 345                 350

Lys Gln Gln Glu Leu Phe Arg Gln Ala Ile Arg Asn Ile Asn Pro Ser
    355                 360                 365

Thr Ala Asn Ala Pro Lys Cys Gln Glu Leu Ala Leu Arg Ser Gln Leu
    370                 375                 380

Pro Thr Leu Glu Gln Asp Gly Gly Thr Pro Asn Ala Val Ser Ser Pro
385                 390                 395                 400

Gly Met Ser Gln Glu Leu Arg Thr Met Thr Thr Asn Ser Ser Asp Pro
            405                 410                 415

Phe Leu Asn Ser Gly Thr Tyr His Ser Arg Asp Glu Ser Thr Asp Ser
            420                 425                 430

Gly Leu Ser Met Ser Ser Tyr Ser Ile Pro Arg Thr Pro Asp Asp Phe
        435                 440                 445

Leu Asn Ser Val Asp Glu Met Asp Thr Gly Asp Thr Ile Ser Gln Ser
    450                 455                 460

Thr Leu Pro Ser Gln Gln Ser Arg Phe Pro Asp Tyr Leu Glu Ala Leu
465                 470                 475                 480

Pro Gly Thr Asn Val Asp Leu Gly Thr Leu Glu Gly Asp Ala Met Asn
            485                 490                 495

Ile Glu Gly Glu Glu Leu Met Pro Ser Leu Gln Glu Ala Leu Ser Ser
            500                 505                 510

Glu Ile Leu Asp Val Gly Ser Val Leu Ala Ala Thr Lys Leu Asp Lys
        515                 520                 525

Glu Ser Phe Leu Thr Trp Leu
    530                 535

<210> SEQ ID NO 5
<211> LENGTH: 1566
<212> TYPE: DNA
<213> ORGANISM: Artificial Sequence
<220> FEATURE:
<223> OTHER INFORMATION: Nucleotide sequence encoding fusion protein of
      NANOG and transactivation domain of YAP

<400> SEQUENCE: 5
atgagtgtgg gtcttcctgg tccccacagt ttgcctagtt ctgaggaagc atcgaattct      60
gggaacgcct catcaatgcc tgcagttttt catcccgaga actattcttg cttacaaggg     120
tctgctactg agatgctctg cacagaggct gcctctcctc gcccttcctc tgaagacctg     180

```
cctcttcaag gcagccctga ttcttctacc agtcccaaac aaaagctctc aagtcctgag    240
gctgacaagg gccctgagga ggaggagaac aaggtccttg ccaggaagca gaagatgcgg    300
actgtgttct ctcaggccca gctgtgtgca ctcaaggaca ggtttcagaa gcagaagtac    360
ctcagcctcc agcagatgca agaactctcc tccattctga acctgagcta taagcaggtt    420
aagacctggt ttcaaaacca aaggatgaag tgcaagcggt ggcagaaaaa ccagtggttg    480
aagactagca atggtctgat tcagaagggc tcagcaccag tggagtatcc cagcatccat    540
tgcagctatc cccagggcta tctggtgaac gcatctggaa gcctttccat gtggggcagc    600
cagacttgga ccaaccccaa cttggagcag cagacctgga ccaacccaac ttggaacaac    660
cagacctgga ccaacccaac ttggagcagc aggcctgga ccgctcagtc ctggaacggc    720
cagccttgga atgctgctcc gctccataac ttcggggagg actttctgca gccttacgta    780
cagttgcagc aaaacttctc tgccagtgat ttggaggtga atttggaagc cactagggaa    840
agccatgcgc attttagcac cccacaagcc ttggaattat tcctgaacta ctctgtgact    900
ccaccaggtg aaatagcggc cgcacaggga ggcgtcctgg gtggaggcag ttccaaccag    960
cagcagcaaa tacagctgca gcagttacag atggagaagg agagactgcg gttgaaacaa   1020
caggaattat ttcggcaggc aatacggaat atcaatccca gcacagcaaa tgctccaaaa   1080
tgtcaggaat tagctctgcg cagccagttg cctacactgg agcaggatgg agggactccg   1140
aatgcagtgt cttctcctgg gatgtctcag gaattgagaa caatgacaac caatagttcc   1200
gatccctttc ttaacagtgg cacctatcac tctcgagatg agagcacaga cagcggcctc   1260
agcatgagca gctacagcat ccctcggacc ccagacgact cctcaacag tgtggatgaa   1320 atggatacag agacaccat cagccaaagc accctgccgt cacagcagag ccgcttcccc   1380
gactacctgg aagccctccc tgggacaaat gtggaccttg gcacactgga aggagatgca   1440
atgaacatag aagggagga gctgatgccc agtctgcagg aagcgctgag ttccgaaatc   1500
ttggacgtgg agtctgtgtt ggctgccacc aagctagata agaaagcttt tctcacgtgg   1560
ttatag                                                              1566
```

<210> SEQ ID NO 6
<211> LENGTH: 521
<212> TYPE: PRT
<213> ORGANISM: Artificial Sequence
<220> FEATURE:
<223> OTHER INFORMATION: Fusion protein of NANOG and transactivation
      domain of YAP

<400> SEQUENCE: 6

Met Ser Val Gly Leu Pro Gly Pro His Ser Leu Pro Ser Ser Glu Glu
1               5                   10                  15

Ala Ser Asn Ser Gly Asn Ala Ser Ser Met Pro Ala Val Phe His Pro
                20                  25                  30

Glu Asn Tyr Ser Cys Leu Gln Gly Ser Ala Thr Glu Met Leu Cys Thr
            35                  40                  45

Glu Ala Ala Ser Pro Arg Pro Ser Ser Glu Asp Leu Pro Leu Gln Gly
        50                  55                  60

Ser Pro Asp Ser Ser Thr Ser Pro Lys Gln Lys Leu Ser Ser Pro Glu
65                  70                  75                  80

Ala Asp Lys Gly Pro Glu Glu Glu Glu Asn Lys Val Leu Ala Arg Lys
                85                  90                  95

Gln Lys Met Arg Thr Val Phe Ser Gln Ala Gln Leu Cys Ala Leu Lys

-continued

```
                100                 105                 110
Asp Arg Phe Gln Lys Gln Lys Tyr Leu Ser Leu Gln Gln Met Gln Glu
        115                 120                 125
Leu Ser Ser Ile Leu Asn Leu Ser Tyr Lys Gln Val Lys Thr Trp Phe
130                 135                 140
Gln Asn Gln Arg Met Lys Cys Lys Arg Trp Gln Lys Asn Gln Trp Leu
145                 150                 155                 160
Lys Thr Ser Asn Gly Leu Ile Gln Lys Gly Ser Ala Pro Val Glu Tyr
                165                 170                 175
Pro Ser Ile His Cys Ser Tyr Pro Gln Gly Tyr Leu Val Asn Ala Ser
            180                 185                 190
Gly Ser Leu Ser Met Trp Gly Ser Gln Thr Trp Thr Asn Pro Thr Trp
        195                 200                 205
Ser Ser Gln Thr Trp Thr Asn Pro Thr Trp Asn Asn Gln Thr Trp Thr
    210                 215                 220
Asn Pro Thr Trp Ser Ser Gln Ala Trp Thr Ala Gln Ser Trp Asn Gly
225                 230                 235                 240
Gln Pro Trp Asn Ala Ala Pro Leu His Asn Phe Gly Glu Asp Phe Leu
                245                 250                 255
Gln Pro Tyr Val Gln Leu Gln Asn Phe Ser Ala Ser Asp Leu Glu
            260                 265                 270
Val Asn Leu Glu Ala Thr Arg Glu Ser His Ala His Phe Ser Thr Pro
        275                 280                 285
Gln Ala Leu Glu Leu Phe Leu Asn Tyr Ser Val Thr Pro Pro Gly Glu
    290                 295                 300
Ile Ala Ala Ala Gln Gly Gly Val Leu Gly Gly Ser Ser Asn Gln
305                 310                 315                 320
Gln Gln Gln Ile Gln Leu Gln Gln Leu Gln Met Glu Lys Glu Arg Leu
                325                 330                 335
Arg Leu Lys Gln Gln Glu Leu Phe Arg Gln Ala Ile Arg Asn Ile Asn
            340                 345                 350
Pro Ser Thr Ala Asn Ala Pro Lys Cys Gln Glu Leu Ala Leu Arg Ser
        355                 360                 365
Gln Leu Pro Thr Leu Glu Gln Asp Gly Gly Thr Pro Asn Ala Val Ser
    370                 375                 380
Ser Pro Gly Met Ser Gln Glu Leu Arg Thr Met Thr Thr Asn Ser Ser
385                 390                 395                 400
Asp Pro Phe Leu Asn Ser Gly Thr Tyr His Ser Arg Asp Glu Ser Thr
                405                 410                 415
Asp Ser Gly Leu Ser Met Ser Ser Tyr Ser Ile Pro Arg Thr Pro Asp
            420                 425                 430
Asp Phe Leu Asn Ser Val Asp Glu Met Asp Thr Gly Asp Thr Ile Ser
        435                 440                 445
Gln Ser Thr Leu Pro Ser Gln Gln Ser Arg Phe Pro Asp Tyr Leu Glu
    450                 455                 460
Ala Leu Pro Gly Thr Asn Val Asp Leu Gly Thr Leu Glu Gly Asp Ala
465                 470                 475                 480
Met Asn Ile Glu Gly Glu Glu Leu Met Pro Ser Leu Gln Glu Ala Leu
                485                 490                 495
Ser Ser Glu Ile Leu Asp Val Glu Ser Val Leu Ala Ala Thr Lys Leu
            500                 505                 510
Asp Lys Glu Ser Phe Leu Thr Trp Leu
        515                 520
```

<210> SEQ ID NO 7
<211> LENGTH: 1452
<212> TYPE: DNA
<213> ORGANISM: Artificial Sequence
<220> FEATURE:
<223> OTHER INFORMATION: Nucleotide sequence encoding KLF4

<400> SEQUENCE: 7

| | |
|---|---:|
| atgaggcagc cacctggcga gtctgacatg gctgtcagcg acgctctgct cccgtccttc | 60 |
| tccacgttcg cgtccggccc ggcgggaagg gagaagacac tgcgtccagc aggtgccccg | 120 |
| actaaccgtt ggcgtgagga actctctcac atgaagcgac ttcccccact tcccggccgc | 180 |
| ccctacgacc tggcggcgac ggtggccaca gacctggaga gtggcggagc tggtgcagct | 240 |
| tgcagcagta acaacccggc cctcctagcc cggaggagga ccgaggagtt caacgacctc | 300 |
| ctggacctag actttatcct ttccaactcg ctaacccacc aggaatcggt ggccgccacc | 360 |
| gtgaccacct cggcgtcagc ttcatcctcg tcttccccgg cgagcagcgg ccctgccagc | 420 |
| gcgccctcca cctgcagctt cagctatccg atccgggccg ggggtgaccc gggcgtggct | 480 |
| gccagcaaca caggtggagg ctcctctac agccgagaat ctgcgccacc tcccacggcc | 540 |
| cccttcaacc tggcggacat caatgacgtg agccctcgg gcggcttcgt ggctgagctc | 600 |
| ctgcggccgg agttggaccc agtatacatt ccgccacagc agcctcagcc gccaggtggc | 660 |
| gggctgatgg gcaagtttgt gctgaaggcg tctctgacca cccctggcag cgagtacagc | 720 |
| agcccttcgg tcatcagtgt tagcaaagga agcccagacg gcagccaccc cgtggtagtg | 780 |
| gcgccctaca gcggtggccc gccgcgcatg tgccccaaga ttaagcaaga ggcggtcccg | 840 |
| tcctgcacgg tcagccggtc cctagaggcc catttgagcg ctggacccca gctcagcaac | 900 |
| ggccaccggc caacacaca cgacttcccc ctggggcggc agctccccac caggactacc | 960 |
| cctacactga gtcccgagga actgctgaac agcagggact gtcaccctgg cctgcctctt | 1020 |
| cccccaggat ccatcccca tccggggccc aactaccctc ctttcctgcc agaccagatg | 1080 |
| cagtcacaag tcccctctct ccattatcaa gagctcatgc caccgggttc ctgcctgcca | 1140 |
| gaggagccca gccaaagag gggaagaagg tcgtggcccc ggaaaagaac agccacccac | 1200 |
| acttgtgact atgcaggctg tggcaaaacc tataccaaga gttctcatct caaggcacac | 1260 |
| ctgcgaactc acacaggcga gaaaccttac cactgtgact gggacggctg tgggtggaaa | 1320 |
| ttcgcccgct ccgatgaact gaccaggcac taccgcaaac acacagggca ccggcccttt | 1380 |
| cagtgccaga gtgtgacag ggccttttcc aggtcggacc accttgcctt acacatgaag | 1440 |
| aggcactttt aa | 1452 |

<210> SEQ ID NO 8
<211> LENGTH: 483
<212> TYPE: PRT
<213> ORGANISM: Artificial Sequence
<220> FEATURE:
<223> OTHER INFORMATION: Protein sequence of KLF4

<400> SEQUENCE: 8

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Pro Ala Gly Ala Pro Thr Asn Arg Trp Arg Glu Glu Leu
        35                  40                  45

```
Ser His Met Lys Arg Leu Pro Pro Leu Pro Gly Arg Pro Tyr Asp Leu
    50                  55                  60

Ala Ala Thr Val Ala Thr Asp Leu Glu Ser Gly Ala Gly Ala Ala
65                  70                  75                  80

Cys Ser Ser Asn Asn Pro Ala Leu Leu Ala Arg Arg Glu Thr Glu Glu
                85                  90                  95

Phe Asn Asp Leu Leu Asp Leu Asp Phe Ile Leu Ser Asn Ser Leu Thr
                100                 105                 110

His Gln Glu Ser Val Ala Ala Thr Val Thr Thr Ser Ala Ser Ala Ser
            115                 120                 125

Ser Ser Ser Ser Pro Ala Ser Ser Gly Pro Ala Ser Ala Pro Ser Thr
            130                 135                 140

Cys Ser Phe Ser Tyr Pro Ile Arg Ala Gly Gly Asp Pro Gly Val Ala
145                 150                 155                 160

Ala Ser Asn Thr Gly Gly Leu Leu Tyr Ser Arg Glu Ser Ala Pro
                165                 170                 175

Pro Pro Thr Ala Pro Phe Asn Leu Ala Asp Ile Asn Asp Val Ser Pro
                180                 185                 190

Ser Gly Gly Phe Val Ala Glu Leu Leu Arg Pro Glu Leu Asp Pro Val
        195                 200                 205

Tyr Ile Pro Pro Gln Gln Pro Gln Pro Gly Gly Gly Leu Met Gly
        210                 215                 220

Lys Phe Val Leu Lys Ala Ser Leu Thr Thr Pro Gly Ser Glu Tyr Ser
225                 230                 235                 240

Ser Pro Ser Val Ile Ser Val Ser Lys Gly Ser Pro Asp Gly Ser His
                245                 250                 255

Pro Val Val Val Ala Pro Tyr Ser Gly Gly Pro Pro Arg Met Cys Pro
                260                 265                 270

Lys Ile Lys Gln Glu Ala Val Pro Ser Cys Thr Val Ser Arg Ser Leu
            275                 280                 285

Glu Ala His Leu Ser Ala Gly Pro Gln Leu Ser Asn Gly His Arg Pro
        290                 295                 300

Asn Thr His Asp Phe Pro Leu Gly Arg Gln Leu Pro Thr Arg Thr Thr
305                 310                 315                 320

Pro Thr Leu Ser Pro Glu Glu Leu Leu Asn Ser Arg Asp Cys His Pro
                325                 330                 335

Gly Leu Pro Leu Pro Pro Gly Phe His Pro His Pro Gly Pro Asn Tyr
                340                 345                 350

Pro Pro Phe Leu Pro Asp Gln Met Gln Ser Gln Val Pro Ser Leu His
            355                 360                 365

Tyr Gln Glu Leu Met Pro Pro Gly Ser Cys Leu Pro Glu Glu Pro Lys
        370                 375                 380

Pro Lys Arg Gly Arg Arg Ser Trp Pro Arg Lys Arg Thr Ala Thr His
385                 390                 395                 400

Thr Cys Asp Tyr Ala Gly Cys Gly Lys Thr Tyr Thr Lys Ser Ser His
                405                 410                 415

Leu Lys Ala His Leu Arg Thr His Thr Gly Glu Lys Pro Tyr His Cys
            420                 425                 430

Asp Trp Asp Gly Cys Gly Trp Lys Phe Ala Arg Ser Asp Glu Leu Thr
        435                 440                 445

Arg His Tyr Arg Lys His Thr Gly His Arg Pro Phe Gln Cys Gln Lys
    450                 455                 460
```

```
Cys Asp Arg Ala Phe Ser Arg Ser Asp His Leu Ala Leu His Met Lys
465                 470                 475                 480

Arg His Phe
```

<210> SEQ ID NO 9
<211> LENGTH: 642
<212> TYPE: DNA
<213> ORGANISM: Artificial Sequence
<220> FEATURE:
<223> OTHER INFORMATION: Nucleotide sequence encoding transactivation
      domain of YAP

<400> SEQUENCE: 9

```
cagggaggcg tcctgggtgg aggcagttcc aaccagcagc agcaaataca gctgcagcag    60
ttacagatgg agaaggagag actgcggttg aaacaacagg aattatttcg gcaggcaata   120
cggaatatca atcccagcac agcaaatgct ccaaaatgtc aggaattagc tctgcgcagc   180
cagttgccta cactggagca ggatggaggg actccgaatg cagtgtcttc tcctgggatg   240
tctcaggaat tgagaacaat gacaaccaat agttccgatc cctttcttaa cagtggcacc   300
tatcactctc gagatgagag cacagacagc ggcctcagca tgagcagcta cagcatccct   360
cggaccccag acgacttcct caacagtgtg atgaaatgg atacaggaga ccatcagc     420 caaagcaccc tgccgtcaca gcagagccgc ttccccgact acctggaagc cctccctggg   480
acaaatgtgg accttggcac actggaagga gatgcaatga acatagaagg ggaggagctg   540
atgcccagtc tgcaggaagc gctgagttcc gaaatcttgg acgtggagtc tgtgttggct   600
gccaccaagc tagataaaga aagctttctc acgtggttat ag                     642
```

<210> SEQ ID NO 10
<211> LENGTH: 213
<212> TYPE: PRT
<213> ORGANISM: Artificial Sequence
<220> FEATURE:
<223> OTHER INFORMATION: Transactivation domain of YAP

<400> SEQUENCE: 10

```
Gln Gly Gly Val Leu Gly Gly Ser Ser Asn Gln Gln Gln Ile
1               5                   10                  15

Gln Leu Gln Gln Leu Gln Met Glu Lys Glu Arg Leu Arg Leu Lys Gln
                20                  25                  30

Gln Glu Leu Phe Arg Gln Ala Ile Arg Asn Ile Asn Pro Ser Thr Ala
            35                  40                  45

Asn Ala Pro Lys Cys Gln Glu Leu Ala Leu Arg Ser Gln Leu Pro Thr
        50                  55                  60

Leu Glu Gln Asp Gly Gly Thr Pro Asn Ala Val Ser Ser Pro Gly Met
65                  70                  75                  80

Ser Gln Glu Leu Arg Thr Met Thr Thr Asn Ser Ser Asp Pro Phe Leu
                85                  90                  95

Asn Ser Gly Thr Tyr His Ser Arg Asp Glu Ser Thr Asp Ser Gly Leu
            100                 105                 110

Ser Met Ser Ser Tyr Ser Ile Pro Arg Thr Pro Asp Asp Phe Leu Asn
        115                 120                 125

Ser Val Asp Glu Met Asp Thr Gly Asp Thr Ile Ser Gln Ser Thr Leu
    130                 135                 140

Pro Ser Gln Gln Ser Arg Phe Pro Asp Tyr Leu Glu Ala Leu Pro Gly
145                 150                 155                 160

Thr Asn Val Asp Leu Gly Thr Leu Glu Gly Asp Ala Met Asn Ile Glu
```

|  |  | 165 |  |  |  | 170 |  |  |  | 175 |  |
| --- | --- | --- | --- | --- | --- | --- | --- | --- | --- | --- | --- |

Gly Glu Glu Leu Met Pro Ser Leu Gln Glu Ala Leu Ser Ser Glu Ile
            180                 185                 190

Leu Asp Val Glu Ser Val Leu Ala Ala Thr Lys Leu Asp Lys Glu Ser
            195                 200                 205

Phe Leu Thr Trp Leu
    210

<210> SEQ ID NO 11
<211> LENGTH: 4673
<212> TYPE: DNA
<213> ORGANISM: Artificial Sequence
<220> FEATURE:
<223> OTHER INFORMATION: Nucleotide sequence of pMXs vector

<400> SEQUENCE: 11

| | |
|---|---|
| cccgaaaagt gccacctgca taatgaaaga ccccacctgt aggtttggca agctagctta | 60 |
| agtaacgcca ttttgcaagg catggaaaaa tacataactg agaatagaaa agttcagatc | 120 |
| aaggtcagga acagatggaa cagctgaata tgggccaaac aggatatctg tggtaagcag | 180 |
| ttcctgcccc ggctcagggc caagaacaga tggaacagct gaatatgggc caaacaggat | 240 |
| atctgtggta agcagttcct gccccggctc agggccaaga acagatggtc ccagatgcg | 300 |
| gtccagccct cagcagtttc tagagaacca tcagatgttt ccagggtgcc caaggacct | 360 |
| gaaatgaccc tgtgccttat ttgaactaac caatcagttc gcttctcgct tctgttcgcg | 420 |
| cgcttctgct ccccgagctc aataaaagag cccacaaccc ctcactcggc gcgccagtga | 480 |
| ttgactgagt cgcccgggta cccgtgtatc caataaaccc tcttgcagtt gcatccgact | 540 |
| tgtggtctcg ctgttccttg ggagggtctc ctctgagtga ttgactaccc gtcagcgggg | 600 |
| gtctttcatt tgggggctcg tccgggatcg ggagacccct gcccagggac caccgaccca | 660 |
| ccaccgggac ctaagctggc cagcaactta tctgtgtctg tccgattgtc tagtgtctat | 720 |
| cactgatttt atccgcctgc gtcggtacta gttagctaac tagctctgta tctggcggac | 780 |
| ccgtggtgga actgacgagt tcggaacacc cggccgcaac cctggagac gtcccaggga | 840 |
| cttcggggggc cgtttttgtg gcccgacctg agtccaaaaa tcccgatcgt tttggactct | 900 |
| ttggtgcacc cccctaatag gagggatatg tggttctggt aggagacgag aacctaaaac | 960 |
| agttcccgcc tccgtctgaa tttttgcttt cggtttggga ccgaagccgc gccgcgcgtc | 1020 |
| ttgtctgctg cagcatcgtt ctgtgttgtc tctgtctgac tgtgtttctg tatttgtctg | 1080 |
| aaaattaggg ccagactgtt accactccct taagtttgac cttacctcac tggaaagatg | 1140 |
| tcgagcggat cgctcacaac cagtcggtag atgtcaagaa gagacgttgg gttaccttct | 1200 |
| gctctgcaga atggccaacc tttaacgtcg gatggccgcg agacggcacc tttaaccgag | 1260 |
| acctcatcac ccaggttaag atcaaggtct tttcacctgg cccgcatgga cacccagacc | 1320 |
| aggtcccta catcgtgacc tgggaagcct tggcttttga cccccctccc tgggtcaagc | 1380 |
| cctttgtaca ccctaagcct ccgcctcctc ttcctccatc cgccccgtct ctccccttg | 1440 |
| aacctcctcg ttcgaccccg cctcgatcct ccctttatcc agccctcact ccttctctag | 1500 |
| gcgccccat atggccatat gagatcttat atggggcacc cccgccccttt gtaaacttcc | 1560 |
| ctgaccctga catgacaaga gttactaaca gcccctctct ccaagctcac ttacaggctc | 1620 |
| tctacttagt ccagcacgaa gtctggagac tctggcggc agcctaccaa gaacaactgg | 1680 |
| accgaccggt ggtacctcac ccttaccgag tcggcgacac agtgtgggtc cgccgacacc | 1740 |

-continued

```
agactaagaa cctagaacct cgctggaaag gaccttacac agtcctgctg accaccccca   1800
ccgcccctcaa agtagacggc atcgcagctt ggatacacgc cgcccacgtg aaggctgccg   1860
accccggggg tggaccatcc tctagactgc cggatctagc tagttaatta aggatcccag   1920
tgtggtggta cggaattcc aactttgtac aaaaaagcag ctacccagc tttcttgtac     1980
aaagttggtg cggccgccag cacagtggtc gacgataaaa taaaagattt tatttagtct   2040
ccagaaaaag gggggaatga agacccccac ctgtaggttt ggcaagctag cttaagtaac   2100
gccattttgc aaggcatgga aaatacata actgagaata gagaagttca gatcaaggtc    2160
aggaacagat ggaacagctg aatatgggcc aaacaggata tctgtggtaa gcagttcctg   2220
ccccggctca gggccaagaa cagatggaac agctgaatat gggccaaaca ggatatctgt   2280
ggtaagcagt tcctgcccccg gctcagggcc aagaacagat ggtccccaga tgcggtccag  2340
ccctcagcag tttctagaga accatcagat gtttccaggg tgccccaagg acctgaaatg   2400
accctgtgcc ttatttgaac taaccaatca gttcgcttct cgcttctgtt cgcgcgcttc    2460
tgctccccga gctcaataaa agagcccaca acccctcact cggggcgcca gtcctccgat   2520
tgactgagtc gcccgggtac ccgtgtatcc aataaaccct cttgcagttg catccgactt   2580
gtggtctcgc tgttccttgg gagggtctcc tctgagtgat tgactacccg tcagcggggg  2640
tctttcacat gcagcatgta tcaaaattaa tttggttttt tttcttaagt atttacatta    2700
aatggccata gttgcattaa tgaatcgcc aacgcgcggg gagaggcggt ttgcgtattg    2760
ggcgctcttc cgcttcctcg ctcactgact cgctgcgctc ggtcgttcgg ctgcggcgag   2820
cggtatcagc tcactcaaag gcggtaatac ggttatccac agaatcaggg gataacgcag    2880
gaaagaacat gtgagcaaaa ggccagcaaa aggccaggaa ccgtaaaaag gccgcgttgc    2940
tggcgttttt ccataggctc cgcccccctg acgagcatca caaaaatcga cgctcaagtc    3000
agaggtggcg aaacccgaca ggactataaa gataccaggc gtttccccct ggaagctccc    3060
tcgtgcgctc tcctgttccg accctgccgc ttaccggata cctgtccgcc tttctccctt     3120
cgggaagcgt ggcgctttct catagctcac gctgtaggta tctcagttcg gtgtaggtcg    3180
ttcgctccaa gctgggctgt gtgcacgaac cccccgttca gcccgaccgc tgcgccttat     3240
ccggtaacta tcgtcttgag tccaacccgg taagacacga cttatcgcca ctggcagcag    3300
ccactggtaa caggattagc agagcgaggt atgtaggcgg tgctacagag ttcttgaagt    3360
ggtggcctaa ctacggctac actagaagaa cagtatttgg tatctgcgct ctgctgaagc    3420
cagttacctt cggaaaaaga gttggtagct cttgatccgg caaacaaacc accgctggta    3480
gcggtggttt ttttgtttgc aagcagcaga ttacgcgcag aaaaaaagga tctcaagaag    3540
atcctttgat cttttctacg gggtctgacg ctcagtggaa cgaaaactca cgttaaggga    3600
ttttggtcat gagattatca aaaaggatct tcacctagat ccttttgcgg ccggccgcaa    3660
atcaatctaa agtatatatg agtaaacttg gtctgacagt taccaatgct taatcagtga    3720
ggcacctatc tcagcgatct gtctatttcg ttcatccata gttgcctgac tccccgtcgt    3780
gtagataact acgatacggg agggcttacc atctggcccc agtgctgcaa tgataccgcg    3840
agacccacgc tcaccggctc cagatttatc agcaataaac cagccagccg aagggccga    3900
gcgcagaagt ggtcctgcaa ctttatccgc ctccatccag tctattaatt gttgccggga    3960
agctagagta agtagttcgc cagttaatag tttgcgcaac gttgttgcca ttgctacagg    4020
catcgtggtg tcacgctcgt cgtttggtat ggcttcattc agctccggtt cccaacgatc    4080
aaggcgagtt acatgatccc ccatgttgtg caaaaaagcg gttagctcct tcggtcctcc    4140
```

```
gatcgttgtc agaagtaagt tggccgcagt gttatcactc atggttatgg cagcactgca    4200
taattctctt actgtcatgc catccgtaag atgcttttct gtgactggtg agtactcaac    4260
caagtcattc tgagaatagt gtatgcggcg accgagttgc tcttgcccgg cgtcaatacg    4320
ggataatacc gcgccacata gcagaacttt aaaagtgctc atcattggaa aacgttcttc    4380
ggggcgaaaa ctctcaagga tcttaccgct gttgagatcc agttcgatgt aacccactcg    4440
tgcacccaac tgatcttcag catcttttac tttcaccagc gtttctgggt gagcaaaaac    4500
aggaaggcaa aatgccgcaa aaaagggaat aagggcgaca cggaaatgtt gaatactcat    4560
actcttcctt tttcaatatt attgaagcat ttatcagggt tattgtctca tgagcggata    4620
catatttgaa tgtatttaga aaataaaca aatagggggtt ccgcgcacat ttc            4673

<210> SEQ ID NO 12
<211> LENGTH: 20
<212> TYPE: DNA
<213> ORGANISM: Artificial Sequence
<220> FEATURE:
<223> OTHER INFORMATION: Forward primer for OCT4

<400> SEQUENCE: 12
taggtgagcc gtctttccac                                                  20

<210> SEQ ID NO 13
<211> LENGTH: 20
<212> TYPE: DNA
<213> ORGANISM: Artificial Sequence
<220> FEATURE:
<223> OTHER INFORMATION: Reverse primer for OCT4

<400> SEQUENCE: 13
gcttagccag gttcgaggat                                                  20

<210> SEQ ID NO 14
<211> LENGTH: 20
<212> TYPE: DNA
<213> ORGANISM: Artificial Sequence
<220> FEATURE:
<223> OTHER INFORMATION: Forward primer for SOX2

<400> SEQUENCE: 14
agggctggga gaaagaagag                                                  20

<210> SEQ ID NO 15
<211> LENGTH: 20
<212> TYPE: DNA
<213> ORGANISM: Artificial Sequence
<220> FEATURE:
<223> OTHER INFORMATION: Reverse primer for SOX2

<400> SEQUENCE: 15
ccgcgattgt tgtgattagt                                                  20

<210> SEQ ID NO 16
<211> LENGTH: 20
<212> TYPE: DNA
<213> ORGANISM: Artificial Sequence
<220> FEATURE:
<223> OTHER INFORMATION: Forward primer for NANOG2

<400> SEQUENCE: 16
atcccttccc tcgccatcac                                                  20
```

```
<210> SEQ ID NO 17
<211> LENGTH: 19
<212> TYPE: DNA
<213> ORGANISM: Artificial Sequence
<220> FEATURE:
<223> OTHER INFORMATION: Reverse primer for NANOG2

<400> SEQUENCE: 17
ggcattgatg aggcgttcc                                            19

<210> SEQ ID NO 18
<211> LENGTH: 24
<212> TYPE: DNA
<213> ORGANISM: Artificial Sequence
<220> FEATURE:
<223> OTHER INFORMATION: Forward primer for Dax1

<400> SEQUENCE: 18
tgctgcggtc caggccatca agag                                      24

<210> SEQ ID NO 19
<211> LENGTH: 24
<212> TYPE: DNA
<213> ORGANISM: Artificial Sequence
<220> FEATURE:
<223> OTHER INFORMATION: Reverse primer for Dax1

<400> SEQUENCE: 19
gggcactgtt cagttcagcg gatc                                      24

<210> SEQ ID NO 20
<211> LENGTH: 23
<212> TYPE: DNA
<213> ORGANISM: Artificial Sequence
<220> FEATURE:
<223> OTHER INFORMATION: Forward primer for Eras

<400> SEQUENCE: 20
tgcctacaaa gtctagcatc ttg                                       23

<210> SEQ ID NO 21
<211> LENGTH: 22
<212> TYPE: DNA
<213> ORGANISM: Artificial Sequence
<220> FEATURE:
<223> OTHER INFORMATION: Reverse primer for Eras

<400> SEQUENCE: 21
cttttaccaa caccacttgc ac                                        22

<210> SEQ ID NO 22
<211> LENGTH: 22
<212> TYPE: DNA
<213> ORGANISM: Artificial Sequence
<220> FEATURE:
<223> OTHER INFORMATION: Forward primer for GAPDH

<400> SEQUENCE: 22
agtcaaggcc gagaatggga ag                                        22

<210> SEQ ID NO 23
<211> LENGTH: 22
<212> TYPE: DNA
<213> ORGANISM: Artificial Sequence
<220> FEATURE:
<223> OTHER INFORMATION: Reverse primer for GAPDH
```

```
<400> SEQUENCE: 23
aagcagttgg tggtgcagga tg                                              22

<210> SEQ ID NO 24
<211> LENGTH: 20
<212> TYPE: DNA
<213> ORGANISM: Artificial Sequence
<220> FEATURE:
<223> OTHER INFORMATION: Forward primer for OCT4

<400> SEQUENCE: 24
gggtggacca tcctctagac                                                 20

<210> SEQ ID NO 25
<211> LENGTH: 18
<212> TYPE: DNA
<213> ORGANISM: Artificial Sequence
<220> FEATURE:
<223> OTHER INFORMATION: Reverse primer for OCT4

<400> SEQUENCE: 25
ccaggttcga gaatccac                                                   18

<210> SEQ ID NO 26
<211> LENGTH: 20
<212> TYPE: DNA
<213> ORGANISM: Artificial Sequence
<220> FEATURE:
<223> OTHER INFORMATION: Forward primer for SOX2

<400> SEQUENCE: 26
gggtggacca tcctctagac                                                 20

<210> SEQ ID NO 27
<211> LENGTH: 18
<212> TYPE: DNA
<213> ORGANISM: Artificial Sequence
<220> FEATURE:
<223> OTHER INFORMATION: Reverse primer for SOX2

<400> SEQUENCE: 27
gggctgttct tctggttg                                                   18

<210> SEQ ID NO 28
<211> LENGTH: 20
<212> TYPE: DNA
<213> ORGANISM: Artificial Sequence
<220> FEATURE:
<223> OTHER INFORMATION: Forward primer for NANOG

<400> SEQUENCE: 28
gggtggacca tcctctagac                                                 20

<210> SEQ ID NO 29
<211> LENGTH: 19
<212> TYPE: DNA
<213> ORGANISM: Artificial Sequence
<220> FEATURE:
<223> OTHER INFORMATION: Reverse primer for NANOG

<400> SEQUENCE: 29
ggcattgatg aggcgttcc                                                  19

<210> SEQ ID NO 30
```

```
<211> LENGTH: 20
<212> TYPE: DNA
<213> ORGANISM: Artificial Sequence
<220> FEATURE:
<223> OTHER INFORMATION: Forward primer for KLF4

<400> SEQUENCE: 30
gggtggacca tcctctagac                                                  20

<210> SEQ ID NO 31
<211> LENGTH: 20
<212> TYPE: DNA
<213> ORGANISM: Artificial Sequence
<220> FEATURE:
<223> OTHER INFORMATION: Reverse primer for KLF4

<400> SEQUENCE: 31
gctggacgca gtgtcttctc                                                  20

<210> SEQ ID NO 32
<211> LENGTH: 22
<212> TYPE: DNA
<213> ORGANISM: Artificial Sequence
<220> FEATURE:
<223> OTHER INFORMATION: Forward primer for GAPDH

<400> SEQUENCE: 32
agtcaaggcc gagaatggga ag                                               22

<210> SEQ ID NO 33
<211> LENGTH: 22
<212> TYPE: DNA
<213> ORGANISM: Artificial Sequence
<220> FEATURE:
<223> OTHER INFORMATION: Reverse primer for GAPDH

<400> SEQUENCE: 33
aagcagttgg tggtgcagga tg                                               22

<210> SEQ ID NO 34
<211> LENGTH: 30
<212> TYPE: DNA
<213> ORGANISM: Artificial Sequence
<220> FEATURE:
<223> OTHER INFORMATION: Forward primer for NANOG promoter

<400> SEQUENCE: 34
gattttgtag gtgggattaa ttgtgaattt                                       30

<210> SEQ ID NO 35
<211> LENGTH: 30
<212> TYPE: DNA
<213> ORGANISM: Artificial Sequence
<220> FEATURE:
<223> OTHER INFORMATION: Reverse primer for NANOG promoter

<400> SEQUENCE: 35
accaaaaaaa cccacactca tatcaatata                                       30

<210> SEQ ID NO 36
<211> LENGTH: 26
<212> TYPE: DNA
<213> ORGANISM: Artificial Sequence
<220> FEATURE:
<223> OTHER INFORMATION: Forward primer for OCT4 promoter

<400> SEQUENCE: 36
```

```
atgggttgaa atattgggtt tattta                                          26
```

<210> SEQ ID NO 37
<211> LENGTH: 25
<212> TYPE: DNA
<213> ORGANISM: Artificial Sequence
<220> FEATURE:
<223> OTHER INFORMATION: Reverse primer for OCT4 promoter

<400> SEQUENCE: 37

```
ccaccctcta accttaacct ctaac                                           25
```

<210> SEQ ID NO 38
<211> LENGTH: 531
<212> TYPE: PRT
<213> ORGANISM: Artificial Sequence
<220> FEATURE:
<223> OTHER INFORMATION: Fusion protein of MyoD and transactivation domain of YAP

<400> SEQUENCE: 38

```
Met Glu Leu Leu Ser Pro Pro Leu Arg Asp Ile Asp Leu Thr Gly Pro
1               5                   10                  15

Asp Gly Ser Leu Cys Ser Phe Glu Thr Ala Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Val His Met Gly Ala Leu Leu Lys Pro Glu Glu His Ala His
        50                  55                  60

Phe Pro Thr Ala Val His Pro Gly Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Ser Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Pro Arg Arg Gln Asn Gly
    210                 215                 220

Tyr Asp Thr Ala Tyr Tyr Ser Glu Ala Ala Arg Glu Ser Arg Pro Gly
225                 230                 235                 240

Lys Ser Ala Ala Val Ser Ser Leu Asp Cys Leu Ser Ser Ile Val Glu
                245                 250                 255

Arg Ile Ser Thr Asp Ser Pro Ala Ala Pro Ala Leu Leu Leu Ala Asp
            260                 265                 270

Ala Pro Pro Glu Ser Pro Pro Gly Pro Pro Glu Gly Ala Ser Leu Ser
        275                 280                 285
```

-continued

Asp Thr Glu Gln Gly Thr Gln Thr Pro Ser Pro Asp Ala Ala Pro Gln
    290                 295                 300

Cys Pro Ala Gly Ser Asn Pro Asn Ala Ile Tyr Gln Val Leu Gln Gly
305                 310                 315                 320

Gly Val Leu Gly Gly Ser Ser Asn Gln Gln Gln Ile Gln Leu
                325                 330                 335

Gln Gln Leu Gln Met Glu Lys Glu Arg Leu Arg Leu Lys Gln Gln Glu
            340                 345                 350

Leu Phe Arg Gln Ala Ile Arg Asn Ile Asn Pro Ser Thr Ala Asn Ala
        355                 360                 365

Pro Lys Cys Gln Glu Leu Ala Leu Arg Ser Gln Leu Pro Thr Leu Glu
    370                 375                 380

Gln Asp Gly Gly Thr Pro Asn Ala Val Ser Ser Pro Gly Met Ser Gln
385                 390                 395                 400

Glu Leu Arg Thr Met Thr Thr Asn Ser Ser Asp Pro Phe Leu Asn Ser
                405                 410                 415

Gly Thr Tyr His Ser Arg Asp Glu Ser Thr Asp Ser Gly Leu Ser Met
            420                 425                 430

Ser Ser Tyr Ser Ile Pro Arg Thr Pro Asp Asp Phe Leu Asn Ser Val
        435                 440                 445

Asp Glu Met Asp Thr Gly Asp Thr Ile Ser Gln Ser Thr Leu Pro Ser
    450                 455                 460

Gln Gln Ser Arg Phe Pro Asp Tyr Leu Glu Ala Leu Pro Gly Thr Asn
465                 470                 475                 480

Val Asp Leu Gly Thr Leu Glu Gly Asp Ala Met Asn Ile Glu Gly Glu
                485                 490                 495

Glu Leu Met Pro Ser Leu Gln Glu Ala Leu Ser Ser Glu Ile Leu Asp
            500                 505                 510

Val Glu Ser Val Leu Ala Ala Thr Lys Leu Asp Lys Glu Ser Phe Leu
        515                 520                 525

Thr Trp Leu
    530

<210> SEQ ID NO 39
<211> LENGTH: 609
<212> TYPE: PRT
<213> ORGANISM: Artificial Sequence
<220> FEATURE:
<223> OTHER INFORMATION: Fusion protein of CEBP alpha and
      transactivation domain of YAP

<400> SEQUENCE: 39

Met Arg Gly Arg Glu Pro Val Gly Ala Leu Gly Gly Arg Arg Arg Gln
1               5                   10                  15

Arg Arg His Ala Gln Ala Gly Gly Arg Arg Gly Ser Pro Cys Arg Glu
            20                  25                  30

Asn Ser Asn Ser Pro Met Glu Ser Ala Asp Phe Tyr Glu Val Glu Pro
        35                  40                  45

Arg Pro Pro Met Ser Ser His Leu Gln Ser Pro His Ala Pro Ser
    50                  55                  60

Asn Ala Ala Phe Gly Phe Pro Arg Gly Ala Gly Pro Ala Pro Pro Pro
65                  70                  75                  80

Ala Pro Pro Ala Ala Pro Glu Pro Leu Gly Gly Ile Cys Glu His Glu
                85                  90                  95

Thr Ser Ile Asp Ile Ser Ala Tyr Ile Asp Pro Ala Ala Phe Asn Asp

```
            100                 105                 110
Glu Phe Leu Ala Asp Leu Phe Gln His Ser Arg Gln Gln Glu Lys Ala
        115                 120                 125

Lys Ala Ala Ala Gly Pro Ala Gly Gly Gly Asp Phe Asp Tyr Pro
130                 135                 140

Gly Ala Pro Ala Gly Pro Gly Gly Ala Val Met Ser Ala Gly Ala His
145                 150                 155                 160

Gly Pro Pro Pro Gly Tyr Gly Cys Ala Ala Gly Tyr Leu Asp Gly
                165                 170                 175

Arg Leu Glu Pro Leu Tyr Glu Arg Val Gly Ala Pro Ala Leu Arg Pro
                180                 185                 190

Leu Val Ile Lys Gln Glu Pro Arg Glu Glu Asp Glu Ala Lys Gln Leu
        195                 200                 205

Ala Leu Ala Gly Leu Phe Pro Tyr Gln Pro Pro Pro Pro Pro Pro
210                 215                 220

Pro His Pro His Ala Ser Pro Ala His Leu Ala Ala Pro His Leu Gln
225                 230                 235                 240

Phe Gln Ile Ala His Cys Gly Gln Thr Thr Met His Leu Gln Pro Gly
                245                 250                 255

His Pro Thr Pro Pro Thr Pro Val Pro Ser Pro His Ala Ala Pro
                260                 265                 270

Ala Leu Gly Ala Ala Gly Leu Pro Gly Pro Gly Ser Ala Leu Lys Gly
                275                 280                 285

Leu Ala Gly Ala His Pro Asp Leu Arg Thr Gly Gly Gly Gly Gly
        290                 295                 300

Ser Gly Ala Gly Ala Gly Lys Ala Lys Lys Ser Val Asp Lys Asn Ser
305                 310                 315                 320

Asn Glu Tyr Arg Val Arg Arg Glu Arg Asn Asn Ile Ala Val Arg Lys
                325                 330                 335

Ser Arg Asp Lys Ala Lys Gln Arg Asn Val Glu Thr Gln Gln Lys Val
                340                 345                 350

Leu Glu Leu Thr Ser Asp Asn Asp Arg Leu Arg Lys Arg Val Glu Gln
                355                 360                 365

Leu Ser Arg Glu Leu Asp Thr Leu Arg Gly Ile Phe Arg Gln Leu Pro
        370                 375                 380

Glu Ser Ser Leu Val Lys Ala Met Gly Asn Cys Ala Gln Gly Gly Val
385                 390                 395                 400

Leu Gly Gly Gly Ser Ser Asn Gln Gln Gln Gln Ile Gln Leu Gln Gln
                405                 410                 415

Leu Gln Met Glu Lys Glu Arg Leu Arg Leu Lys Gln Gln Glu Leu Phe
                420                 425                 430

Arg Gln Ala Ile Arg Asn Ile Asn Pro Ser Thr Ala Asn Ala Pro Lys
                435                 440                 445

Cys Gln Glu Leu Ala Leu Arg Ser Gln Leu Pro Thr Leu Glu Gln Asp
        450                 455                 460

Gly Gly Thr Pro Asn Ala Val Ser Ser Pro Gly Met Ser Gln Glu Leu
465                 470                 475                 480

Arg Thr Met Thr Thr Asn Ser Ser Asp Pro Phe Leu Asn Ser Gly Thr
                485                 490                 495

Tyr His Ser Arg Asp Glu Ser Thr Asp Ser Gly Leu Ser Met Ser Ser
                500                 505                 510

Tyr Ser Ile Pro Arg Thr Pro Asp Asp Phe Leu Asn Ser Val Asp Glu
        515                 520                 525
```

```
Met Asp Thr Gly Asp Thr Ile Ser Gln Ser Leu Pro Ser Gln Gln
530                 535                 540

Ser Arg Phe Pro Asp Tyr Leu Glu Ala Leu Pro Gly Thr Asn Val Asp
545                 550                 555                 560

Leu Gly Thr Leu Glu Gly Asp Ala Met Asn Ile Glu Gly Glu Leu
                565                 570                 575

Met Pro Ser Leu Gln Glu Ala Leu Ser Ser Glu Ile Leu Asp Val Glu
                580                 585                 590

Ser Val Leu Ala Ala Thr Lys Leu Asp Lys Glu Ser Phe Leu Thr Trp
                595                 600                 605

Leu

<210> SEQ ID NO 40
<211> LENGTH: 604
<212> TYPE: PRT
<213> ORGANISM: Artificial Sequence
<220> FEATURE:
<223> OTHER INFORMATION: Fusion protein of Pax5 and transactivation
      domain of YAP

<400> SEQUENCE: 40

Met Asp Leu Glu Lys Asn Tyr Pro Thr Pro Arg Thr Ile Arg Thr Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270
```

-continued

Gly Leu Asp Asp Met Lys Ala Asn Leu Thr Ser Pro Thr Pro Ala Asp
            275                 280                 285

Ile Gly Ser Ser Val Pro Gly Pro Gln Ser Tyr Pro Ile Val Thr Gly
        290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Ser
            340                 345                 350

Ser Tyr Asn Asp Ser Trp Arg Phe Pro Asn Pro Gly Leu Leu Gly Ser
        355                 360                 365

Pro Tyr Tyr Tyr Ser Pro Ala Ala Arg Gly Ala Ala Pro Pro Ala Ala
    370                 375                 380

Ala Thr Ala Tyr Asp Arg His Gln Gly Gly Val Leu Gly Gly Gly Ser
385                 390                 395                 400

Ser Asn Gln Gln Gln Gln Ile Gln Leu Gln Leu Gln Met Glu Lys
                405                 410                 415

Glu Arg Leu Arg Leu Lys Gln Gln Glu Leu Phe Arg Gln Ala Ile Arg
            420                 425                 430

Asn Ile Asn Pro Ser Thr Ala Asn Ala Pro Lys Cys Gln Glu Leu Ala
        435                 440                 445

Leu Arg Ser Gln Leu Pro Thr Leu Glu Gln Asp Gly Gly Thr Pro Asn
    450                 455                 460

Ala Val Ser Ser Pro Gly Met Ser Gln Glu Leu Arg Thr Met Thr Thr
465                 470                 475                 480

Asn Ser Ser Asp Pro Phe Leu Asn Ser Gly Thr Tyr His Ser Arg Asp
                485                 490                 495

Glu Ser Thr Asp Ser Gly Leu Ser Met Ser Ser Tyr Ser Ile Pro Arg
            500                 505                 510

Thr Pro Asp Asp Phe Leu Asn Ser Val Asp Glu Met Asp Thr Gly Asp
        515                 520                 525

Thr Ile Ser Gln Ser Thr Leu Pro Ser Gln Gln Ser Arg Phe Pro Asp
    530                 535                 540

Tyr Leu Glu Ala Leu Pro Gly Thr Asn Val Asp Leu Gly Thr Leu Glu
545                 550                 555                 560

Gly Asp Ala Met Asn Ile Glu Gly Glu Glu Leu Met Pro Ser Leu Gln
                565                 570                 575

Glu Ala Leu Ser Ser Glu Ile Leu Asp Val Glu Ser Val Leu Ala Ala
            580                 585                 590

Thr Lys Leu Asp Lys Glu Ser Phe Leu Thr Trp Leu
        595                 600

<210> SEQ ID NO 41
<211> LENGTH: 496
<212> TYPE: PRT
<213> ORGANISM: Artificial Sequence
<220> FEATURE:
<223> OTHER INFORMATION: Fusion protein of Pdx1 and transactivation
      domain of YAP

<400> SEQUENCE: 41

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro

-continued

```
                 20                  25                  30
Pro Ala Cys Leu Tyr Met Gly Arg Gln Pro Pro Pro Pro His
             35                  40                  45
Pro Phe Pro Gly Ala Leu Gly Ala Leu Glu Gln Gly Ser Pro Pro Asp
 50                  55                  60
Ile Ser Pro Tyr Glu Val Pro Pro Leu Ala Asp Asp Pro Ala Val Ala
 65                  70                  75                  80
His Leu His His His Leu Pro Ala Gln Leu Ala Leu Pro His Pro Pro
                 85                  90                  95
Ala Gly Pro Phe Pro Glu Gly Ala Glu Pro Gly Val Leu Glu Glu Pro
                100                 105                 110
Asn Arg Val Gln Leu Pro Phe Pro Trp Met Lys Ser Thr Lys Ala His
                115                 120                 125
Ala Trp Lys Gly Gln Trp Ala Gly Gly Ala Tyr Ala Ala Glu Pro Glu
                130                 135                 140
Glu Asn Lys Arg Thr Arg Thr Ala Tyr Thr Arg Ala Gln Leu Leu Glu
145                 150                 155                 160
Leu Glu Lys Glu Phe Leu Phe Asn Lys Tyr Ile Ser Arg Pro Arg Arg
                165                 170                 175
Val Glu Leu Ala Val Met Leu Asn Leu Thr Glu Arg His Ile Lys Ile
                180                 185                 190
Trp Phe Gln Asn Arg Arg Met Lys Trp Lys Lys Glu Glu Asp Lys Lys
                195                 200                 205
Arg Gly Gly Gly Thr Ala Val Gly Gly Gly Val Ala Glu Pro Glu
                210                 215                 220
Gln Asp Cys Ala Val Thr Ser Gly Glu Glu Leu Leu Ala Leu Pro Pro
225                 230                 235                 240
Pro Pro Pro Pro Gly Gly Ala Val Pro Ala Ala Pro Val Ala Ala
                245                 250                 255
Arg Glu Gly Arg Leu Pro Pro Gly Leu Ser Ala Ser Pro Gln Pro Ser
                260                 265                 270
Ser Val Ala Pro Arg Arg Pro Gln Glu Pro Arg Gln Gly Gly Val Leu
                275                 280                 285
Gly Gly Gly Ser Ser Asn Gln Gln Gln Ile Gln Leu Gln Gln Leu
                290                 295                 300
Gln Met Glu Lys Glu Arg Leu Arg Leu Lys Gln Gln Glu Leu Phe Arg
305                 310                 315                 320
Gln Ala Ile Arg Asn Ile Asn Pro Ser Thr Ala Asn Ala Pro Lys Cys
                325                 330                 335
Gln Glu Leu Ala Leu Arg Ser Gln Leu Pro Thr Leu Glu Gln Asp Gly
                340                 345                 350
Gly Thr Pro Asn Ala Val Ser Ser Pro Gly Met Ser Gln Glu Leu Arg
                355                 360                 365
Thr Met Thr Thr Asn Ser Ser Asp Pro Phe Leu Asn Ser Gly Thr Tyr
                370                 375                 380
His Ser Arg Asp Glu Ser Thr Asp Ser Gly Leu Ser Met Ser Ser Tyr
385                 390                 395                 400
Ser Ile Pro Arg Thr Pro Asp Asp Phe Leu Asn Ser Val Asp Glu Met
                405                 410                 415
Asp Thr Gly Asp Thr Ile Ser Gln Ser Thr Leu Pro Ser Gln Gln Ser
                420                 425                 430
Arg Phe Pro Asp Tyr Leu Glu Ala Leu Pro Gly Thr Asn Val Asp Leu
                435                 440                 445
```

Gly Thr Leu Glu Gly Asp Ala Met Asn Ile Glu Gly Glu Glu Leu Met
        450                 455                 460

Pro Ser Leu Gln Glu Ala Leu Ser Ser Glu Ile Leu Asp Val Glu Ser
465                 470                 475                 480

Val Leu Ala Ala Thr Lys Leu Asp Lys Glu Ser Phe Leu Thr Trp Leu
                485                 490                 495

<210> SEQ ID NO 42
<211> LENGTH: 427
<212> TYPE: PRT
<213> ORGANISM: Artificial Sequence
<220> FEATURE:
<223> OTHER INFORMATION: Fusion protein of Ngn3 and transactivation
      domain of YAP

<400> SEQUENCE: 42

Met Ala Pro His Pro Leu Asp Ala Leu Thr Ile Gln Val Ser Pro Glu
1               5                   10                  15

Thr Gln Gln Pro Phe Pro Gly Ala Ser Asp His Glu Val Leu Ser Ser
            20                  25                  30

Asn Ser Thr Pro Pro Ser Pro Thr Leu Ile Pro Arg Asp Cys Ser Glu
        35                  40                  45

Ala Glu Val Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu Gln Gly Gly Val Leu Gly Gly Gly Ser Ser
    210                 215                 220

Asn Gln Gln Gln Gln Ile Gln Leu Gln Leu Gln Met Glu Lys Glu
225                 230                 235                 240

Arg Leu Arg Leu Lys Gln Gln Glu Leu Phe Arg Gln Ala Ile Arg Asn
                245                 250                 255

Ile Asn Pro Ser Thr Ala Asn Ala Pro Lys Cys Gln Glu Leu Ala Leu
            260                 265                 270

Arg Ser Gln Leu Pro Thr Leu Glu Gln Asp Gly Gly Thr Pro Asn Ala
        275                 280                 285

Val Ser Ser Pro Gly Met Ser Gln Glu Leu Arg Thr Met Thr Thr Asn
    290                 295                 300

Ser Ser Asp Pro Phe Leu Asn Ser Gly Thr Tyr His Ser Arg Asp Glu

```
                305                 310                 315                 320
Ser Thr Asp Ser Gly Leu Ser Met Ser Ser Tyr Ser Ile Pro Arg Thr
                    325                 330                 335

Pro Asp Asp Phe Leu Asn Ser Val Asp Glu Met Asp Thr Gly Asp Thr
                340                 345                 350

Ile Ser Gln Ser Thr Leu Pro Ser Gln Gln Ser Arg Phe Pro Asp Tyr
                355                 360                 365

Leu Glu Ala Leu Pro Gly Thr Asn Val Asp Leu Gly Thr Leu Glu Gly
            370                 375                 380

Asp Ala Met Asn Ile Glu Gly Glu Leu Met Pro Ser Leu Gln Glu
385                 390                 395                 400

Ala Leu Ser Ser Glu Ile Leu Asp Val Glu Ser Val Leu Ala Ala Thr
                405                 410                 415

Lys Leu Asp Lys Glu Ser Phe Leu Thr Trp Leu
                420                 425

<210> SEQ ID NO 43
<211> LENGTH: 572
<212> TYPE: PRT
<213> ORGANISM: Artificial Sequence
<220> FEATURE:
<223> OTHER INFORMATION: Fusion protein of MafA and transactivation
      domain of YAP

<400> SEQUENCE: 43

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
                20                  25                  30

Lys Glu Pro Pro Glu Ala Glu Arg Phe Cys His Arg Leu Pro Pro Gly
            35                  40                  45

Ser Leu Ser Ser Thr Pro Leu Ser Thr Pro Cys Ser Ser Val Pro Ser
        50                  55                  60

Ser Pro Ser Phe Cys Ala Pro Ser Pro Gly Thr Gly Gly Ala Gly
65                  70                  75                  80

Gly Gly Gly Ser Ala Ala Gln Ala Gly Ala Pro Gly Pro Pro Ser
                85                  90                  95

Gly Gly Pro Gly Thr Val Gly Gly Ala Ser Gly Lys Ala Val Leu Glu
            100                 105                 110

Asp Leu Tyr Trp Met Ser Gly Tyr Gln His His Leu Asn Pro Glu Ala
        115                 120                 125

Leu Asn Leu Thr Pro Glu Asp Ala Val Glu Ala Leu Ile Gly Ser Gly
    130                 135                 140

His His Gly Ala His His Gly Ala His His Pro Ala Ala Ala Ala
145                 150                 155                 160

Tyr Glu Ala Phe Arg Gly Gln Ser Phe Ala Gly Gly Gly Gly Ala Asp
                165                 170                 175

Asp Met Gly Ala Gly His His Gly Ala His Thr Ala His His
            180                 185                 190

His His Ser Ala His His His His His His His Gly Gly
        195                 200                 205

Ser Gly His His Gly Gly Gly Ala Gly His Gly Gly Gly Ala Gly
    210                 215                 220

His His Val Arg Leu Glu Glu Arg Phe Ser Asp Asp Gln Leu Val Ser
225                 230                 235                 240
```

-continued

```
Met Ser Val Arg Glu Leu Asn Arg Gln Leu Arg Gly Phe Ser Lys Glu
            245                 250                 255

Glu Val Ile Arg Leu Lys Gln Lys Arg Arg Thr Leu Lys Asn Arg Gly
        260                 265                 270

Tyr Ala Gln Ser Cys Arg Phe Lys Arg Val Gln Gln Arg His Ile Leu
    275                 280                 285

Glu Ser Glu Lys Cys Gln Leu Gln Ser Gln Val Glu Gln Leu Lys Leu
290                 295                 300

Glu Val Gly Arg Leu Ala Lys Glu Arg Asp Leu Tyr Lys Glu Lys Tyr
305                 310                 315                 320

Glu Lys Leu Ala Gly Arg Gly Gly Pro Gly Gly Ala Gly Gly Ala Gly
                325                 330                 335

Phe Pro Arg Glu Pro Ser Pro Ala Gln Ala Gly Pro Gly Ala Ala Lys
            340                 345                 350

Gly Ala Pro Asp Phe Phe Leu Gln Gly Val Leu Gly Gly Gly Ser
        355                 360                 365

Ser Asn Gln Gln Gln Ile Gln Leu Gln Gln Leu Gln Met Glu Lys
    370                 375                 380

Glu Arg Leu Arg Leu Lys Gln Gln Glu Leu Phe Arg Gln Ala Ile Arg
385                 390                 395                 400

Asn Ile Asn Pro Ser Thr Ala Asn Ala Pro Lys Cys Gln Glu Leu Ala
                405                 410                 415

Leu Arg Ser Gln Leu Pro Thr Leu Glu Gln Asp Gly Gly Thr Pro Asn
            420                 425                 430

Ala Val Ser Ser Pro Gly Met Ser Gln Glu Leu Arg Thr Met Thr Thr
        435                 440                 445

Asn Ser Ser Asp Pro Phe Leu Asn Ser Gly Thr Tyr His Ser Arg Asp
    450                 455                 460

Glu Ser Thr Asp Ser Gly Leu Ser Met Ser Ser Tyr Ser Ile Pro Arg
465                 470                 475                 480

Thr Pro Asp Asp Phe Leu Asn Ser Val Asp Glu Met Asp Thr Gly Asp
                485                 490                 495

Thr Ile Ser Gln Ser Thr Leu Pro Ser Gln Gln Ser Arg Phe Pro Asp
            500                 505                 510

Tyr Leu Glu Ala Leu Pro Gly Thr Asn Val Asp Leu Gly Thr Leu Glu
        515                 520                 525

Gly Asp Ala Met Asn Ile Glu Gly Glu Leu Met Pro Ser Leu Gln
    530                 535                 540

Glu Ala Leu Ser Ser Glu Ile Leu Asp Val Glu Ser Val Leu Ala Ala
545                 550                 555                 560

Thr Lys Leu Asp Lys Glu Ser Phe Leu Thr Trp Leu
                565                 570
```

<210> SEQ ID NO 44
<211> LENGTH: 444
<212> TYPE: PRT
<213> ORGANISM: Artificial Sequence
<220> FEATURE:
<223> OTHER INFORMATION: Fusion protein of Ascl1 and transactivation domain of YAP

<400> SEQUENCE: 44

```
Met Glu Ser Ser Gly Lys Met Glu Ser Gly Ala Gly Gln Gln Pro Gln
1               5                   10                  15

Pro Pro Gln Pro Phe Leu Pro Pro Ala Ala Cys Phe Phe Ala Thr Ala
            20                  25                  30
```

```
Ala Ala Ala Ala Ala Ala Ala Ala Ala Gln Ser Ala Gln Gln
        35                  40                  45
Gln Gln Pro Gln Ala Pro Pro Gln Ala Pro Gln Leu Ser Pro Val
50                  55                  60
Ala Asp Ser Gln Pro Ser Gly Gly His Lys Ser Ala Ala Lys Gln
65                  70                  75                  80
Val Lys Arg Gln Arg Ser Ser Pro Glu Leu Met Arg Cys Lys Arg
                85                  90                  95
Arg Leu Asn Phe Ser Gly Phe Gly Tyr Ser Leu Pro Gln Gln Gln Pro
            100                 105                 110
Ala Ala Val Ala Arg Arg Asn Glu Arg Glu Arg Asn Arg Val Lys Leu
            115                 120                 125
Val Asn Leu Gly Phe Ala Thr Leu Arg Glu His Val Pro Asn Gly Ala
    130                 135                 140
Ala Asn Lys Lys Met Ser Lys Val Glu Thr Leu Arg Ser Ala Val Glu
145                 150                 155                 160
Tyr Ile Arg Ala Leu Gln Gln Leu Leu Asp Glu His Asp Ala Val Ser
                165                 170                 175
Ala Ala Phe Gln Ala Gly Val Leu Ser Pro Thr Ile Ser Pro Asn Tyr
            180                 185                 190
Ser Asn Asp Leu Asn Ser Met Ala Gly Ser Pro Val Ser Ser Tyr Ser
        195                 200                 205
Ser Asp Glu Gly Ser Tyr Asp Pro Leu Ser Pro Glu Glu Gln Glu Leu
    210                 215                 220
Leu Asp Phe Thr Asn Trp Phe Gln Gly Val Leu Gly Gly Gly Ser
225                 230                 235                 240
Ser Asn Gln Gln Gln Gln Ile Gln Leu Gln Gln Leu Gln Met Glu Lys
                245                 250                 255
Glu Arg Leu Arg Leu Lys Gln Gln Glu Leu Phe Arg Gln Ala Ile Arg
            260                 265                 270
Asn Ile Asn Pro Ser Thr Ala Asn Ala Pro Lys Cys Gln Glu Leu Ala
    275                 280                 285
Leu Arg Ser Gln Leu Pro Thr Leu Glu Gln Asp Gly Gly Thr Pro Asn
    290                 295                 300
Ala Val Ser Ser Pro Gly Met Ser Gln Glu Leu Arg Thr Met Thr Thr
305                 310                 315                 320
Asn Ser Ser Asp Pro Phe Leu Asn Ser Gly Thr Tyr His Ser Arg Asp
                325                 330                 335
Glu Ser Thr Asp Ser Gly Leu Ser Met Ser Ser Tyr Ser Ile Pro Arg
            340                 345                 350
Thr Pro Asp Asp Phe Leu Asn Ser Val Asp Glu Met Thr Gly Asp
    355                 360                 365
Thr Ile Ser Gln Ser Thr Leu Pro Ser Gln Gln Ser Arg Phe Pro Asp
    370                 375                 380
Tyr Leu Glu Ala Leu Pro Gly Thr Asn Val Asp Leu Gly Thr Leu Glu
385                 390                 395                 400
Gly Asp Ala Met Asn Ile Glu Gly Glu Leu Met Pro Ser Leu Gln
                405                 410                 415
Glu Ala Leu Ser Ser Glu Ile Leu Asp Val Glu Ser Val Leu Ala Ala
            420                 425                 430
Thr Lys Leu Asp Lys Glu Ser Phe Leu Thr Trp Leu
    435                 440
```

-continued

```
<210> SEQ ID NO 45
<211> LENGTH: 658
<212> TYPE: PRT
<213> ORGANISM: Artificial Sequence
<220> FEATURE:
<223> OTHER INFORMATION: Fusion protein of Brn2 and transactivation
      domain of YAP

<400> SEQUENCE: 45

Met Ala Thr Ala Ala Ser Asn His Tyr Ser Leu Leu Thr Ser Ser Ala
1               5                   10                  15

Ser Ile Val His Ala Glu Pro Pro Gly Gly Met Gln Gln Gly Ala Gly
            20                  25                  30

Gly Tyr Arg Glu Ala Gln Ser Leu Val Gln Gly Asp Tyr Gly Ala Leu
        35                  40                  45

Gln Ser Asn Gly His Pro Leu Ser His Ala His Gln Trp Ile Thr Ala
    50                  55                  60

Leu Ser His Gly Gly Gly Gly Gly Gly Gly Gly Gly Gly Gly Gly Gly
65                  70                  75                  80

Gly Gly Gly Gly Gly Gly Gly Asp Gly Ser Pro Trp Ser Thr Ser
                85                  90                  95

Pro Leu Gly Gln Pro Asp Ile Lys Pro Ser Val Val Gln Gln Gly
            100                 105                 110

Gly Arg Gly Asp Glu Leu His Gly Pro Gly Ala Leu Gln Gln His
        115                 120                 125

Gln Gln Gln Gln Gln Gln Gln Gln Gln Gln Gln Gln Gln Gln Gln
    130                 135                 140

Gln Gln Gln Gln Gln Gln Arg Pro Pro His Leu Val His His Ala
145                 150                 155                 160

Ala Asn His His Pro Gly Pro Gly Ala Trp Arg Ser Ala Ala Ala
                165                 170                 175

Ala His Leu Pro Pro Ser Met Gly Ala Ser Asn Gly Gly Leu Leu Tyr
            180                 185                 190

Ser Gln Pro Ser Phe Thr Val Asn Gly Met Leu Gly Ala Gly Gly Gln
        195                 200                 205

Pro Ala Gly Leu His His His Gly Leu Arg Asp Ala His Asp Glu Pro
    210                 215                 220

His His Ala Asp His His Pro His Pro Ser His Pro His Gln Gln
225                 230                 235                 240

Pro Pro Pro Pro Pro Pro Gln Gly Pro Pro Gly His Pro Gly Ala
                245                 250                 255

His His Asp Pro His Ser Asp Glu Asp Thr Pro Thr Ser Asp Asp Leu
            260                 265                 270

Glu Gln Phe Ala Lys Gln Phe Lys Gln Arg Arg Ile Lys Leu Gly Phe
        275                 280                 285

Thr Gln Ala Asp Val Gly Leu Ala Leu Gly Thr Leu Tyr Gly Asn Val
    290                 295                 300

Phe Ser Gln Thr Thr Ile Cys Arg Phe Glu Ala Leu Gln Leu Ser Phe
305                 310                 315                 320

Lys Asn Met Cys Lys Leu Lys Pro Leu Leu Asn Lys Trp Leu Glu Glu
                325                 330                 335

Ala Asp Ser Ser Ser Gly Ser Pro Thr Ser Ile Asp Lys Ile Ala Ala
            340                 345                 350

Gln Gly Arg Lys Arg Lys Lys Arg Thr Ser Ile Glu Val Ser Val Lys
        355                 360                 365
```

```
Gly Ala Leu Glu Ser His Phe Leu Lys Cys Pro Lys Pro Ser Ala Gln
    370                 375                 380

Glu Ile Thr Ser Leu Ala Asp Ser Leu Gln Leu Lys Glu Val Val
385                 390                 395                 400

Arg Val Trp Phe Cys Asn Arg Arg Gln Lys Glu Lys Arg Met Thr Pro
                405                 410                 415

Pro Gly Gly Thr Leu Pro Gly Ala Glu Asp Val Tyr Gly Gly Ser Arg
            420                 425                 430

Asp Thr Pro Pro His His Gly Val Gln Thr Pro Val Gln Gln Gly Gly
        435                 440                 445

Val Leu Gly Gly Gly Ser Ser Asn Gln Gln Gln Gln Ile Gln Leu Gln
    450                 455                 460

Gln Leu Gln Met Glu Lys Glu Arg Leu Arg Leu Lys Gln Gln Glu Leu
465                 470                 475                 480

Phe Arg Gln Ala Ile Arg Asn Ile Asn Pro Ser Thr Ala Asn Ala Pro
                485                 490                 495

Lys Cys Gln Glu Leu Ala Leu Arg Ser Gln Leu Pro Thr Leu Glu Gln
            500                 505                 510

Asp Gly Gly Thr Pro Asn Ala Val Ser Ser Pro Gly Met Ser Gln Glu
        515                 520                 525

Leu Arg Thr Met Thr Thr Asn Ser Ser Asp Pro Phe Leu Asn Ser Gly
    530                 535                 540

Thr Tyr His Ser Arg Asp Glu Ser Thr Asp Ser Gly Leu Ser Met Ser
545                 550                 555                 560

Ser Tyr Ser Ile Pro Arg Thr Pro Asp Asp Phe Leu Asn Ser Val Asp
                565                 570                 575

Glu Met Asp Thr Gly Asp Thr Ile Ser Gln Ser Thr Leu Pro Ser Gln
            580                 585                 590

Gln Ser Arg Phe Pro Asp Tyr Leu Glu Ala Leu Pro Gly Thr Asn Val
        595                 600                 605

Asp Leu Gly Thr Leu Glu Gly Asp Ala Met Asn Ile Glu Gly Glu Glu
    610                 615                 620

Leu Met Pro Ser Leu Gln Glu Ala Leu Ser Ser Glu Ile Leu Asp Val
625                 630                 635                 640

Glu Ser Val Leu Ala Ala Thr Lys Leu Asp Lys Glu Ser Phe Leu Thr
                645                 650                 655

Trp Leu

<210> SEQ ID NO 46
<211> LENGTH: 654
<212> TYPE: PRT
<213> ORGANISM: Artificial Sequence
<220> FEATURE:
<223> OTHER INFORMATION: Fusion protein of Gata4 and transactivation
      domain of YAP

<400> SEQUENCE: 46

Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Ser Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Gly Ser Ala Ala Ala Ala Gly
    50                  55                  60
```

```
Thr Thr Ser Gly Gly Ser Ser Gly Ala Gly Pro Ser Gly Ala Gly Pro
 65                  70                  75                  80

Gly Thr Gln Gln Gly Ser Pro Gly Trp Ser Gln Ala Gly Ala Glu Gly
                 85                  90                  95

Ala Ala Tyr Thr Pro Pro Val Ser Pro Arg Phe Ser Phe Pro Gly
            100                 105                 110

Thr Thr Gly Ser Leu Ala Ala Ala Ala Ala Ala Ala Ala Arg Glu
        115                 120                 125

Ala Ala Ala Tyr Gly Ser Gly Gly Ala Gly Ala Gly Leu Ala
130                 135                 140

Gly Arg Glu Gln Tyr Gly Arg Pro Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Gly Arg His Pro Asn Leu Asp Met Phe Asp
        195                 200                 205

Asp Phe Ser Glu Gly Arg Glu Cys Val Asn Cys Gly Ala Met Ser Thr
210                 215                 220

Pro Leu Trp Arg Arg Asp Gly Thr Gly His Tyr Leu Cys Asn Ala Cys
225                 230                 235                 240

Gly Leu Tyr His Lys Met Asn Gly Ile Asn Arg Pro Leu Ile Lys Pro
                245                 250                 255

Gln Arg Arg Leu Ser Ala Ser Arg Arg Val Gly Leu Ser Cys Ala Asn
            260                 265                 270

Cys Gln Thr Thr Thr Thr Thr Leu Trp Arg Arg Asn Ala Glu Gly Glu
        275                 280                 285

Pro Val Cys Asn Ala Cys Gly Leu Tyr Met Lys Leu His Gly Val Pro
290                 295                 300

Arg Pro Leu Ala Met Arg Lys Glu Gly Ile Gln Thr Arg Lys Arg Lys
305                 310                 315                 320

Pro Lys Asn Leu Asn Lys Ser Lys Thr Pro Ala Gly Pro Ala Gly Glu
                325                 330                 335

Thr Leu Pro Pro Ser Ser Gly Ala Ser Ser Gly Asn Ser Ser Asn Ala
            340                 345                 350

Thr Ser Ser Ser Ser Ser Ser Glu Glu Met Arg Pro Ile Lys Thr Glu
        355                 360                 365

Pro Gly Leu Ser Ser His Tyr Gly His Ser Ser Ser Met Ser Gln Thr
370                 375                 380

Phe Ser Thr Val Ser Gly His Gly Pro Ser Ile His Pro Val Leu Ser
385                 390                 395                 400

Ala Leu Lys Leu Ser Pro Gln Gly Tyr Ala Ser Pro Val Thr Gln Thr
                405                 410                 415

Ser Gln Ala Ser Ser Lys Gln Asp Ser Trp Asn Ser Leu Val Leu Ala
            420                 425                 430

Asp Ser His Gly Asp Ile Ile Thr Ala Gln Gly Gly Val Leu Gly Gly
        435                 440                 445

Gly Ser Ser Asn Gln Gln Gln Ile Gln Leu Gln Gln Leu Gln Met
450                 455                 460

Glu Lys Glu Arg Leu Arg Leu Lys Gln Gln Glu Leu Phe Arg Gln Ala
465                 470                 475                 480
```

```
Ile Arg Asn Ile Asn Pro Ser Thr Ala Asn Ala Pro Lys Cys Gln Glu
                485                 490                 495

Leu Ala Leu Arg Ser Gln Leu Pro Thr Leu Glu Gln Asp Gly Gly Thr
            500                 505                 510

Pro Asn Ala Val Ser Ser Pro Gly Met Ser Gln Glu Leu Arg Thr Met
            515                 520                 525

Thr Thr Asn Ser Ser Asp Pro Phe Leu Asn Ser Gly Thr Tyr His Ser
    530                 535                 540

Arg Asp Glu Ser Thr Asp Ser Gly Leu Ser Met Ser Ser Tyr Ser Ile
545                 550                 555                 560

Pro Arg Thr Pro Asp Asp Phe Leu Asn Ser Val Asp Glu Met Asp Thr
                565                 570                 575

Gly Asp Thr Ile Ser Gln Ser Thr Leu Pro Ser Gln Gln Ser Arg Phe
            580                 585                 590

Pro Asp Tyr Leu Glu Ala Leu Pro Gly Thr Asn Val Asp Leu Gly Thr
            595                 600                 605

Leu Glu Gly Asp Ala Met Asn Ile Glu Gly Glu Leu Met Pro Ser
    610                 615                 620

Leu Gln Glu Ala Leu Ser Ser Glu Ile Leu Asp Val Glu Ser Val Leu
625                 630                 635                 640

Ala Ala Thr Lys Leu Asp Lys Glu Ser Phe Leu Thr Trp Leu
                645                 650

<210> SEQ ID NO 47
<211> LENGTH: 679
<212> TYPE: PRT
<213> ORGANISM: Artificial Sequence
<220> FEATURE:
<223> OTHER INFORMATION: Fusion protein of Mef2c and transactivation
      domain of YAP

<400> SEQUENCE: 47

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Thr Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65              70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Ser Phe Glu Met Pro
    130                 135                 140

Val Thr Ile Pro Val Ser Ser His Asn Ser Leu Val Tyr Ser Asn Pro
145                 150                 155                 160

Val Ser Thr Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190
```

```
Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Ile Gln Ala Lys Ser
225                 230                 235                 240

Pro Pro Pro Met Asn Leu Gly Met Asn Arg Lys Pro Asp Leu Arg
                245                 250                 255

Val Leu Ile Pro Pro Gly Ser Lys Asn Thr Met Pro Ser Val Asn Gln
                260                 265                 270

Arg Ile Asn Asn Ser Gln Ser Ala Gln Ser Leu Ala Thr Pro Val Val
            275                 280                 285

Ser Val Ala Thr Pro Thr Leu Pro Gly Gln Gly Met Gly Gly Tyr Pro
        290                 295                 300

Ser Ala Ile Ser Thr Thr Tyr Gly Thr Glu Tyr Ser Leu Ser Ser Ala
305                 310                 315                 320

Asp Leu Ser Ser Leu Ser Gly Phe Asn Thr Ala Ser Ala Leu His Leu
                325                 330                 335

Gly Ser Val Thr Gly Trp Gln Gln Gln His Leu His Asn Met Pro Pro
            340                 345                 350

Ser Ala Leu Ser Gln Leu Gly Ala Cys Thr Ser Thr His Leu Ser Gln
        355                 360                 365

Ser Ser Asn Leu Ser Leu Pro Ser Thr Gln Ser Leu Ser Ile Lys Ser
    370                 375                 380

Glu Pro Val Ser Pro Pro Arg Asp Arg Thr Thr Thr Pro Ser Arg Tyr
385                 390                 395                 400

Pro Gln His Thr Thr Arg His Glu Ala Gly Arg Ser Pro Val Asp Ser
                405                 410                 415

Leu Ser Ser Cys Ser Ser Ser Tyr Asp Gly Ser Asp Arg Glu Asp His
                420                 425                 430

Arg Asn Glu Phe His Ser Pro Ile Gly Leu Thr Arg Pro Ser Pro Asp
            435                 440                 445

Glu Arg Glu Ser Pro Ser Val Lys Arg Met Arg Leu Ser Glu Gly Trp
        450                 455                 460

Ala Thr Gln Gly Gly Val Leu Gly Gly Gly Ser Ser Asn Gln Gln Gln
465                 470                 475                 480

Gln Ile Gln Leu Gln Gln Leu Gln Met Glu Lys Glu Arg Leu Arg Leu
                485                 490                 495

Lys Gln Gln Glu Leu Phe Arg Gln Ala Ile Arg Asn Ile Asn Pro Ser
                500                 505                 510

Thr Ala Asn Ala Pro Lys Cys Gln Glu Leu Ala Leu Arg Ser Gln Leu
            515                 520                 525

Pro Thr Leu Glu Gln Asp Gly Gly Thr Pro Asn Ala Val Ser Ser Pro
        530                 535                 540

Gly Met Ser Gln Glu Leu Arg Thr Met Thr Thr Asn Ser Ser Asp Pro
545                 550                 555                 560

Phe Leu Asn Ser Gly Thr Tyr His Ser Arg Asp Glu Ser Thr Asp Ser
                565                 570                 575

Gly Leu Ser Met Ser Ser Tyr Ser Ile Pro Arg Thr Pro Asp Asp Phe
            580                 585                 590

Leu Asn Ser Val Asp Glu Met Asp Thr Gly Asp Thr Ile Ser Gln Ser
        595                 600                 605
```

Thr Leu Pro Ser Gln Gln Ser Arg Phe Pro Asp Tyr Leu Glu Ala Leu
610                 615                 620

Pro Gly Thr Asn Val Asp Leu Gly Thr Leu Glu Gly Asp Ala Met Asn
625                 630                 635                 640

Ile Glu Gly Glu Leu Met Pro Ser Leu Gln Glu Ala Leu Ser Ser
            645                 650                 655

Glu Ile Leu Asp Val Glu Ser Val Leu Ala Ala Thr Lys Leu Asp Lys
            660                 665                 670

Glu Ser Phe Leu Thr Trp Leu
            675

<210> SEQ ID NO 48
<211> LENGTH: 731
<212> TYPE: PRT
<213> ORGANISM: Artificial Sequence
<220> FEATURE:
<223> OTHER INFORMATION: Fusion protein of Tbx5 and transactivation
      domain of YAP

<400> SEQUENCE: 48

Met Ala Asp Thr Asp Glu Gly Phe Gly Leu Ala Arg Thr Pro Leu Glu
1               5                   10                  15

Pro Asp Ser Lys Asp Arg Ser Cys Asp Ser Lys Pro Glu Ser Ala Leu
                20                  25                  30

Gly Ala Pro Ser Lys Ser Pro Ser Ser Pro Gln Ala Ala Phe Thr Gln
            35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
210                 215                 220

Leu Lys Ile Glu Asn Asn Pro Phe Ala Lys Gly Phe Arg Gly Ser Asp
225                 230                 235                 240

Asp Leu Glu Leu His Arg Met Ser Arg Met Gln Ser Lys Glu Tyr Pro
                245                 250                 255

Val Val Pro Arg Ser Thr Val Arg His Lys Val Thr Ser Asn His Ser
            260                 265                 270

Pro Phe Ser Ser Glu Thr Arg Ala Leu Ser Thr Ser Ser Asn Leu Gly
        275                 280                 285

-continued

```
Ser Gln Tyr Gln Cys Glu Asn Gly Val Ser Gly Pro Ser Gln Asp Leu
    290                 295                 300
Leu Pro Pro Asn Pro Tyr Pro Leu Ala Gln Glu His Ser Gln Ile
305                 310                 315                 320
Tyr His Cys Thr Lys Arg Lys Asp Glu Glu Cys Ser Ser Thr Glu His
                325                 330                 335
Pro Tyr Lys Lys Pro Tyr Met Glu Thr Ser Pro Ser Glu Glu Asp Thr
            340                 345                 350
Phe Tyr Arg Ser Gly Tyr Pro Gln Gln Gln Gly Leu Ser Thr Ser Tyr
        355                 360                 365
Arg Thr Glu Ser Ala Gln Arg Gln Ala Cys Met Tyr Ala Ser Ser Ala
370                 375                 380
Pro Pro Ser Glu Pro Val Pro Ser Leu Glu Asp Ile Ser Cys Asn Thr
385                 390                 395                 400
Trp Pro Ser Met Pro Ser Tyr Ser Ser Cys Thr Val Thr Val Gln
                405                 410                 415
Pro Met Asp Arg Leu Pro Tyr Gln His Phe Ser Ala His Phe Thr Ser
            420                 425                 430
Gly Pro Leu Val Pro Arg Leu Ala Gly Met Ala Asn His Gly Ser Pro
        435                 440                 445
Gln Leu Gly Glu Gly Met Phe Gln His Gln Thr Ser Val Ala His Gln
    450                 455                 460
Pro Val Val Arg Gln Cys Gly Pro Gln Thr Gly Leu Gln Ser Pro Gly
465                 470                 475                 480
Gly Leu Gln Pro Pro Glu Phe Leu Tyr Thr His Gly Val Pro Arg Thr
                485                 490                 495
Leu Ser Pro His Gln Tyr His Ser Val His Gly Val Gly Met Val Pro
            500                 505                 510
Glu Trp Ser Glu Asn Ser Gln Gly Gly Val Leu Gly Gly Ser Ser
        515                 520                 525
Asn Gln Gln Gln Gln Ile Gln Leu Gln Leu Gln Met Glu Lys Glu
    530                 535                 540
Arg Leu Arg Leu Lys Gln Gln Glu Leu Phe Arg Gln Ala Ile Arg Asn
545                 550                 555                 560
Ile Asn Pro Ser Thr Ala Asn Ala Pro Lys Cys Gln Glu Leu Ala Leu
                565                 570                 575
Arg Ser Gln Leu Pro Thr Leu Glu Gln Asp Gly Gly Thr Pro Asn Ala
            580                 585                 590
Val Ser Ser Pro Gly Met Ser Gln Glu Leu Arg Thr Met Thr Thr Asn
        595                 600                 605
Ser Ser Asp Pro Phe Leu Asn Ser Gly Thr Tyr His Ser Arg Asp Glu
    610                 615                 620
Ser Thr Asp Ser Gly Leu Ser Met Ser Ser Tyr Ser Ile Pro Arg Thr
625                 630                 635                 640
Pro Asp Asp Phe Leu Asn Ser Val Asp Glu Met Asp Thr Gly Asp Thr
                645                 650                 655
Ile Ser Gln Ser Thr Leu Pro Ser Gln Gln Ser Arg Phe Pro Asp Tyr
            660                 665                 670
Leu Glu Ala Leu Pro Gly Thr Asn Val Asp Leu Gly Thr Leu Glu Gly
        675                 680                 685
Asp Ala Met Asn Ile Glu Gly Glu Glu Leu Met Pro Ser Leu Gln Glu
    690                 695                 700
```

Ala Leu Ser Ser Glu Ile Leu Asp Val Glu Ser Val Leu Ala Ala Thr
705                 710                 715                 720

Lys Leu Asp Lys Glu Ser Phe Leu Thr Trp Leu
                725                 730

<210> SEQ ID NO 49
<211> LENGTH: 1596
<212> TYPE: DNA
<213> ORGANISM: Artificial Sequence
<220> FEATURE:
<223> OTHER INFORMATION: Nucleotide sequence encoding fusion protein of
      MyoD and transactivation domain of YAP

<400> SEQUENCE: 49

```
atggagcttc tatcgccgcc actccgggac atagacttga caggccccga cggctctctc    60
tgctcctttg agacagcaga cgacttctat gatgacccgt gtttcgactc accagacctg   120
cgcttttttg aggacctgga cccgcgcctg gtgcacatgg agccctcct gaaaccggag    180
gagcacgcac acttccctac tgcggtgcac ccaggcccag cgctcgtga ggatgagcat    240
gtgcgcgcgc ccagcgggca ccaccaggcg ggtcgctgct tgctgtgggc ctgcaaggcg   300
tgcaagcgca agaccaccaa cgctgatcgc cgcaaggccg ccaccatgcg cgagcgccgc   360
cgcctgagca agtgaatga ggccttcgag acgctcaagc gctgcacgtc cagcaacccg   420
aaccagcggc tacccaaggt ggagatcctg cgcaacgcca tccgctacat cgaaggtctg   480
caggctctgc tgcgcgacca ggacgccgcg ccccctggcg ccgctgcctt ctacgcacct   540
ggaccgctgc ccccaggccg tgcagcgag cactacagtg gcgactcaga tgcatccagc   600
ccgcgctcca actgctctga tggcatgatg gattacagcg gccccccaag cggccccgg    660
cggcagaatg gctacgacac cgcctactac agtgaggcgg cgcgcgagtc caggccaggg   720
aagagtgcgg ctgtgtcgag cctcgactgc ctgtccagca tagtggagcg catctccaca   780
gacagccccg ctgcgcctgc gctgcttttg gcagatgcac caccagagtc gcctccgggt   840
ccgccagagg gggcatccct aagcgacaca gaacagggaa cccagacccc gtctcccgac   900
gccgccctc agtgtcctgc aggctcaaac cccaatgcga tttatcaggt gcttcaggga   960
ggcgtcctgg gtggaggcag ttccaaccag cagcagcaaa tacagctgca gcagttacag  1020
atggagaagg agagactgcg gttgaaacaa caggaattat tcggcaggc aatacggaat   1080
atcaatccca gcacagcaaa tgctccaaaa tgtcaggaat tagctctgcg cagccagttg  1140
cctacactgg agcaggatgg agggactccg aatgcagtgt cttctcctgg gatgtctcag  1200
gaattgagaa caatgacaac caatagttcc gatccctttc ttaacagtgg cacctatcac  1260
tctcgagatg agagcacaga cagcggcctc agcatgagca gctacagcat ccctcggacc  1320
ccagacgact tcctcaacag tgtggatgaa atggatacag agacaccat cagccaaagc  1380
accctgccgt cacagcagag ccgcttcccc gactacctgg aagccctccc tgggacaaat  1440
gtggaccttg gcacactgga aggagatgca atgaacatag aaggggagga gctgatgccc  1500
agtctgcagg aagcgctgag ttccgaaatc ttggacgtgg agtctgtgtt ggctgccacc  1560
aagctagata agaaagctt tctcacgtgg ttatag                              1596
```

<210> SEQ ID NO 50
<211> LENGTH: 1830
<212> TYPE: DNA
<213> ORGANISM: Artificial Sequence
<220> FEATURE:
<223> OTHER INFORMATION: Nucleotide sequence encoding fusion protein of
      CEBP alpha and transactivation domain of YAP

<400> SEQUENCE: 50

```
ctgcgcgggc gcgagccagt tgggg cactg ggtgggcggc ggcgacagcg gcgccacgcg    60
caggctggag ccgccgagg ctcgccatgc cgggagaact ctaactcccc catggagtcg    120
gccgacttct acgaggtgga gccgcggccc ccgatgagca gtcacctcca gagcccccg    180
cacgcgccca gcaacgccgc ctttggcttt ccccggggcg cgggccccgc gccgccccca    240
gccccacctg ccgccccgga gccgctgggc ggcatctgcg agcacgagac gtctatagac    300
atcagcgcct acatcgaccc ggccgccttc aacgacgagt tcctggccga cctcttccag    360
cacagccgac agcaggagaa ggccaaggcg cggcgggcc ccgcgggtgg cggcggtgac    420
tttgactacc cgggagcccc ggcgggcccc ggcggcgcgg tcatgtccgc ggggggcgcac    480
gggccccctc ccggctacgg ctgtgcgcg ccggctacc tggacggcag gctggagccc    540
ctgtacgagc gcgtcggggc gcccgcgcta cggccgctgg tgatcaaaca agagccccgc    600
gaggaggacg aggcgaagca gctggcgctg gccggcctct tccctacca gccaccgccg    660
ccaccgccac cgccgcaccc gcacgcgtct cccgcgcacc tggccgcccc ccacttgcag    720
ttccagatcg cgcactgcgg ccagaccacc atgcacctgc agcctggcca ccccacaccg    780
ccgcccacgc ccgtgcccag cccgcacgct gcgcccgcct gggtgctgc gggcctgcct    840
ggccccggga gcgcgctcaa gggcttggcc ggtgcgcacc ccgacctccg cacgggaggc    900
ggcggcggtg gcagcggtgc cggtgcgggc aaagccaaga agtcggtgga caagaacagc    960
aacgagtacc gggtacggcg ggaacgcaac aacatcgcgg tgcgcaagag ccgagataaa   1020
gccaaacaac gcaacgtgga gacgcaacag aaggtgctgg agttgaccag tgacaatgac   1080
cgcctgcgca gcgggtgga acagctgagc cgtgaactgg acgcgctgcg gggcatcttc   1140
cgccagctgc ctgagagctc cttggtcaag gccatgggca actgcgcgca gggaggcgtc   1200
ctgggtggag gcagttccaa ccagcagcag caaatacagc tgcagcagtt acagatggag   1260
aaggagagac tgcggttgaa acaacaggaa ttatttcggc aggcaatacg gaatatcaat   1320
cccagcacag caaatgctcc aaaatgtcag gaattagctc tgcgcagcca gttgcctaca   1380
ctggagcagg atggagggac tccgaatgca gtgtcttctc ctgggatgtc tcaggaattg   1440
agaacaatga caaccaatag ttccgatccc tttcttaaca gtggcaccta tcactctcga   1500
gatgagagca cagacagcgg cctcagcatg agcagctaca gcatccctcg gaccccagac   1560
gacttcctca acagtgtgga tgaaatggat acaggagaca ccatcagcca agcaccctg   1620
ccgtcacagc agagccgctt ccccgactac ctggaagccc tccctgggac aaatgtggac   1680
cttggcacac tggaaggaga tgcaatgaac atagaagggg aggagctgat gcccagtctg   1740
caggaagcgc tgagttccga aatcttggac gtggagtctg tgttggctgc caccaagcta   1800
gataaagaaa gctttctcac gtggttatag                                    1830
```

<210> SEQ ID NO 51
<211> LENGTH: 1815
<212> TYPE: DNA
<213> ORGANISM: Artificial Sequence
<220> FEATURE:
<223> OTHER INFORMATION: Nucleotide sequence encoding fusion protein of Pax5 and transactivation domain of YAP

<400> SEQUENCE: 51

```
atggatttag agaaaaatta cccgactcct cggaccatca ggacaggaca tggaggagtg    60
aatcagcttg ggggggtttt tgtgaatgga cggccactcc cagatgtagt ccgccaaagg    120
```

```
atagtggaac ttgcccatca aggtgtcagg ccctgcgaca tctccaggca gcttcgggtc      180
agccatggtt gtgtcagcaa aattcttggc aggtattatg agacaggaag catcaagccg      240
ggggtgattg gaggatccaa accaaaggtt gccactccca aagtggtgga aaaaatcgct      300
gagtacaaac gccaaaaccc taccatgttt gcctgggaga tcaggaccg gctgttggca       360 gagcgagtct gtgacaatga cactgtgccc agcgtcagct ccatcaacag gatcattcgg      420
acaaaagtac agcagccccc caatcagccg gtcccagctt ccagtcacag catagtgtct      480
acaggctccg tgacgcaggt gtcatcggtg agcaccgact ccgcgggctc ctcatactcc      540
atcagtggca tcctgggcat cacgtccccc agtgccgaca ccaacaaacg caagagggat      600
gaaggtattc aggagtctcc agtgccgaat ggccactcac ttccgggccg ggacttcctc      660
cggaagcaga tgcggggaga cctgttcaca cagcagcagc tggaggtgct ggaccgcgtg      720
tttgagagac agcactactc tgacatcttc accaccacgg aacccatcaa gccagaacag      780
accacagagt attcagccat ggcttcactg gctggaggcc tggatgacat gaaagccaac      840 tgacgagcc ccaccccgc tgacatcggg agcagcgttc caggcccaca gtcctaccct        900
attgtcacag gccgagactt ggcgagcaca ccctcccgg gtaccctcc acacgtcccc        960 cccgctggac agggcagcta ctctgcaccg acgctgacag ggatggtgcc tgggagtgaa     1020 tttctggaa gtccctacag ccaccctcag tattcttcct acaatgattc ttggaggttc      1080
cccaacccag ggctgcttgg ctccccatac tattacagcc ctgcagcccg aggagcggcc     1140
ccaccggccg cagccaccgc ctatgaccgt caccagggag gcgtcctggg tggaggcagt     1200
tccaaccagc agcagcaaat acagctgcag cagttacaga tggagaagga gagactgcgg     1260
ttgaaacaac aggaattatt tcggcaggca atacggaata tcaatcccag cacagcaaat     1320
gctccaaaat gtcaggaatt agctctgcgc agccagttgc ctacactgga gcaggatgga     1380
gggactccga atgcagtgtc ttctcctggg atgtctcagg aattgagaac aatgacaacc     1440
aatagttccg atcccttcct taacagtggc acctatcact ctcgagatga gagcacagac     1500
agcggcctca gcatgagcag ctacagcatc cctcggaccc cagacgactt cctcaacagt     1560
gtggatgaaa tggatacagg agacaccatc agccaaagca ccctgccgtc acagcagagc     1620
cgcttccccg actacctgga agccctccct gggacaaatg tggaccttgg cacactggaa     1680
ggagatgcaa tgaacataga aggggaggag ctgatgccca gtctgcagga agcgctgagt     1740
tccgaaatct tggacgtgga gtctgtgttg gctgccacca gctagataa agaaagcttt      1800 ctcacgtggt tatag                                                     1815
```

<210> SEQ ID NO 52
<211> LENGTH: 1491
<212> TYPE: DNA
<213> ORGANISM: Artificial Sequence
<220> FEATURE:
<223> OTHER INFORMATION: Nucleotide sequence encoding fusion protein of
      Pdx1 and transactivation domain of YAP

<400> SEQUENCE: 52

```
atgaacggcg aggagcagta ctacgcggcc acgcagcttt acaaggaccc atgcgcgttc       60
cagcgaggcc cggcgccgga gttcagcgcc agccccctg cgtgcctgta catgggccgc       120 cagccccgc cgccgccgcc gcacccgttc cctggcgccc tgggcgcgct ggagcagggc       180 agcccccgg acatctcccc gtacgaggtg cccccctcg ccgacgaccc cgcggtggcg       240
caccttcacc accacctccc ggctcagctc gcgctccccc acccgccgc cgggcccttc       300
```

-continued

| | |
|---|---|
| ccggagggag ccgagccggg cgtcctggag gagcccaacc gcgtccagct gcctttccca | 360 |
| tggatgaagt ctaccaaagc tcacgcgtgg aaaggccagt gggcaggcgg cgcctacgct | 420 |
| gcggagccgg aggagaacaa gcggacgcgc acggcctaca cgcgcgcaca gctgctagag | 480 |
| ctggagaagg agttcctatt caacaagtac atctcacggc cgcgccgggt ggagctggct | 540 |
| gtcatgttga acttgaccga gagacacatc aagatctggt tccaaaaccg ccgcatgaag | 600 |
| tggaaaaagg aggaggacaa gaagcgcggc ggcgggacag ctgtcggggg tggcggggtc | 660 |
| gcggagcctg agcaggactg cgccgtgacc tccggcgagg agcttctggc gctgccgccg | 720 |
| ccgccgcccc ccgaggtgc tgtgccgccc gctgccccg ttgccgcccg agagggccgc | 780 |
| ctgccgcctg gccttagcgc gtcgccacag ccctccagcg tcgcgcctcg gcggccgcag | 840 |
| gaaccacgac agggaggcgt cctgggtgga ggcagttcca accagcagca gcaaatacag | 900 |
| ctgcagcagt tacagatgga aaggagaga ctgcggttga acaacagga attatttcgg | 960 |
| caggcaatac ggaatatcaa tcccagcaca gcaaatgctc caaaatgtca ggaattagct | 1020 |
| ctgcgcagcc agttgcctac actggagcag gatggaggga ctccgaatgc agtgtcttct | 1080 |
| cctgggatgt ctcaggaatt gagaacaatg acaaccaata gttccgatcc ctttcttaac | 1140 |
| agtggcacct atcactctcg agatgagagc acagacagcg gcctcagcat gagcagctac | 1200 |
| agcatccctc ggaccccaga cgacttcctc aacagtgtgg atgaaatgga tagggagac | 1260 |
| accatcagcc aaagcaccct gccgtcacag cagagccgct tccccgacta cctggaagcc | 1320 |
| ctccctggga caaatgtgga ccttggcaca ctggaaggag atgcaatgaa catagaaggg | 1380 |
| gaggagctga tgcccagtct gcaggaagcg ctgagttccg aaatcttgga cgtggagtct | 1440 |
| gtgttggctg ccaccaagct agataaagaa gctttctca cgtggttata g | 1491 |

<210> SEQ ID NO 53
<211> LENGTH: 1284
<212> TYPE: DNA
<213> ORGANISM: Artificial Sequence
<220> FEATURE:
<223> OTHER INFORMATION: Nucleotide sequence encoding fusion protein of Ngn3 and transactivation domain of YAP

<400> SEQUENCE: 53

| | |
|---|---|
| atggcgcctc atcccttgga tgcgctcacc atccaagtgt ccccagagac acaacaacct | 60 |
| tttcccggag cctcggacca cgaagtgctc agttccaatt ccaccccacc tagccccact | 120 |
| ctcataccta gggactgctc cgaagcagaa gtgggtgact gccgagggac ctcgaggaag | 180 |
| ctccgcgccc gacgcggagg gcgcaacagg cccaagagcg agttggcact cagcaaacag | 240 |
| cgaagaagcc ggcgcaagaa ggccaatgat cgggagcgca atcgcatgca caacctcaac | 300 |
| tcggcgctgg atgcgctgcg cggtgtcctg cccaccttcc cggatgacgc caaacttaca | 360 |
| aagatcgaga ccctgcgctt cgcccacaac tacatctggg cactgactca gacgctcgc | 420 |
| atagcggacc acagcttcta tggcccggag cccctgtgc cctgtggaga gctggggagc | 480 |
| cccggaggtg gctccaacgg ggactggggc tctatctact cccccagtctc ccaagcgggt | 540 |
| aacctgagcc ccacgccctc attggaggaa ttccctggcc tgcaggtgcc cagctcccca | 600 |
| tcctatctgc tcccgggagc actggtgttc tcagacttct tgcagggagg cgtcctgggt | 660 |
| ggaggcagtt ccaaccagca gcagcaaata cagctgcagc agttacagat ggagaaggag | 720 |
| agactgcggt tgaacaacag gaattatttt cggcaggcaa tacggaatat caatcccagc | 780 |
| acagcaaatg ctccaaaatg tcaggaatta gctctgcgca gccagttgcc tacactggag | 840 |

```
caggatggag ggactccgaa tgcagtgtct tctcctggga tgtctcagga attgagaaca    900
atgacaacca atagttccga tcccttctt aacagtggca cctatcactc tcgagatgag     960
agcacagaca gcggcctcag catgagcagc tacagcatcc ctcggacccc agacgacttc   1020
ctcaacagtg tggatgaaat ggatacagga gacaccatca gccaaagcac cctgccgtca   1080
cagcagagcc gcttccccga ctacctggaa gccctccctg gacaaatgt ggaccttggc    1140 acactggaag gagatgcaat gaacatagaa ggggaggagc tgatgcccag tctgcaggaa   1200
gcgctgagtt ccgaaatctt ggacgtggag tctgtgttgg ctgccaccaa gctagataaa   1260
gaaagctttc tcacgtggtt atag                                          1284
```

<210> SEQ ID NO 54
<211> LENGTH: 1719
<212> TYPE: DNA
<213> ORGANISM: Artificial Sequence
<220> FEATURE:
<223> OTHER INFORMATION: Nucleotide sequence encoding fusion protein of
      MafA and transactivation domain of YAP

<400> SEQUENCE: 54

```
atggccgcgg agctggcgat gggcgcagag ctgcccagca gcccactggc catcgagtac     60
gtcaacgact tcgacctgat gaagttcgag gtgaagaagg agccgcccga ggccgagcgc   120
ttctgccacc gcctgccgcc cggctcgctg tcctcgacgc ccctcagcac gccctgctcc   180
tcggtgccct cttcgcccag cttctgcgca cccagcccgg gcacaggcgg cggcgcgggc   240 ggcggggca gcgcggctca ggccgggggc gccccggggc gccgagtgg aggcccggc      300 actgtcgggg gcgcctcagg aaaagcggtg ctggaggatc tgtactggat gagcgggtac   360
cagcaccacc tgaaccccga ggcgctcaac ctgacgccgg aggacgcggt ggaggcgctc   420
atcggcagcg ccaccacgg cgcgcaccac ggcgcgcatc acccggcggc tgctgcggcc   480
tatgaggcct tccgggggtca gagcttcgcg ggcggcggcg cgcggacga catgggtgcc   540 ggccaccacc acggcgcaca ccacactgcc caccatcatc actctgccca ccatcaccat   600
caccaccatc accaccacgg aggctctggc caccacggcg gaggcgcggg tcacggcgga   660
ggcggcgcag gccaccacgt gcgcttggag gagcgcttct ccgacgacca gctggtatcc   720
atgtccgtgc gggagctgaa ccggcagctc cgcggcttca gcaaggagga ggtcatccga   780
ctgaaacaga gcggcgcac gctcaagaac cgcggctacg cgcagtcgtg ccgcttcaag   840
cgggtgcagc agcggcacat tctggagagc gagaagtgcc agctccagag ccaggtggag   900
cagctgaagc tggaggtggg gcgtctggcc aaggagcggg acctgtacaa ggagaaatac   960
gagaagttgg cgggccgggg cggcccccggg ggcgcgggcg gggccggctt ccctcgggag  1020
ccctcgccag cgcaggctgg ccccggggcg gccaaggcg cacccgactt ctttctgcag   1080
ggaggcgtcc tgggtggagg cagttccaac cagcagcagc aaatacagct gcagcagtta  1140
cagatggaga aggagagact gcggttgaaa caacaggaat tatttcggca ggcaatacgg  1200
aatatcaatc ccagcacagc aaatgctcca aaatgtcagg aattagctct gcgcagccag  1260
ttgcctacac tggagcagga tggagggact ccgaatgcag tgtcttctcc tgggatgtct  1320
caggaattga aacaatgac aaccaatagt tccgatccct ttcttaacag tggcacctat  1380
cactctcgag atgagagcac agacagcggc ctcagcatga gcagctacag catccctcgg  1440
accccagacg acttcctcaa cagtgtggat gaaatggata caggagacac catcagccaa  1500
agcaccctgc cgtcacagca gagccgcttc cccgactacc tggaagccct ccctgggaca  1560
```

```
aatgtggacc ttggcacact ggaaggagat gcaatgaaca tagaagggga ggagctgatg    1620
cccagtctgc aggaagcgct gagttccgaa atcttggacg tggagtctgt gttggctgcc    1680
accaagctag ataaagaaag ctttctcacg tggttatag                           1719
```

<210> SEQ ID NO 55
<211> LENGTH: 1335
<212> TYPE: DNA
<213> ORGANISM: Artificial Sequence
<220> FEATURE:
<223> OTHER INFORMATION: Nucleotide sequence encoding fusion protein of
      Ascl1 and transactivation domain of YAP

<400> SEQUENCE: 55

```
atggagagct ctggcaagat ggagagtgga gccggccagc agccgcagcc cccgcagccc      60
ttcctgcctc ccgcagcctg cttctttgcg accgcggcgg cggcggcagc ggcggcggcc    120
gcggcagctc agagcgcgca gcagcaacag ccgcaggcgc cgccgcagca ggcgccgcag    180
ctgagcccgg tggccgacag ccagccctca gggggcggtc acaagtcagc ggccaagcag    240
gtcaagcgcc agcgctcgtc ctctccggaa ctgatgcgct gcaaacgccg gctcaacttc    300
agcggcttcg gctacagcct gccacagcag cagccggccg ccgtggcgcg ccgcaacgag    360
cgcgagcgca accgggtcaa gttggtcaac ctgggttttg ccaccctccg ggagcatgtc    420
cccaacggcg cggccaacaa gaagatgagc aaggtggaga cgctgcgctc ggcggtcgag    480
tacatccgcg cgctgcagca gctgctggac gagcacgacg cggtgagcgc tgcctttcag    540
gcgggcgtcc tgtcgcccac catctccccc aactactcca cgacttgaa ctctatggcg     600 ggttctccgg tctcgtccta ctcctccgac gagggatcct acgaccctct tagcccagag    660
gaacaagagc tgctggactt taccaactgg ttccagggag cgtcctggg tggaggcagt     720 tccaaccagc agcagcaaat acagctgcag cagttacaga tggagaagga gagactgcgg    780
ttgaaacaac aggaattatt tcggcaggca atacggaata tcaatcccag cacagcaaat    840
gctccaaaat gtcaggaatt agctctgcgc agccagttgc ctacactgga gcaggatgga    900
gggactccga atgcagtgtc ttctcctggg atgtctcagg aattgagaac aatgacaacc    960
aatagttccg atcccttcct taacagtggc acctatcact ctcgagatga gagcacagac   1020
agcggcctca gcatgagcag ctacagcatc cctcggaccc cagacgactt cctcaacagt   1080
gtggatgaaa tggatacagg agacaccatc agccaaagca ccctgccgtc acagcagagc   1140
cgcttccccg actacctgga agccctccct gggacaaatg tggaccttgg cacactggaa   1200
ggagatgcaa tgaacataga aggggaggag ctgatgccca gtctgcagga agcgctgagt   1260
tccgaaatct tggacgtgga gtctgtgttg ctgccacca agctagataa agaaagcttt    1320
ctcacgtggt tatag                                                    1335
```

<210> SEQ ID NO 56
<211> LENGTH: 1977
<212> TYPE: DNA
<213> ORGANISM: Artificial Sequence
<220> FEATURE:
<223> OTHER INFORMATION: Nucleotide sequence encoding fusion protein of
      Brn2 and transactivation domain of YAP

<400> SEQUENCE: 56

```
atggcgaccg cagcgtctaa ccactacagc ctgctcacct ccagcgcctc catcgtacat      60
gccgagccgc ctggcggcat gcagcagggc gcaggggggct accgcgaggc gcagagcctg    120
```

| | |
|---|---|
| gtgcagggcg actacggcgc gctgcagagc aacgggcacc cgctcagcca cgctcaccag | 180 |
| tggatcaccg cgctgtccca cggcggcggc ggcggggggcg gcggcggcgg tggaggaggc | 240 |
| gggggaggcg gcggggagg cggcgacggc tccccgtggt ccaccagccc cctaggccag | 300 |
| ccggacatca agccctcggt ggtggtacag cagggtggcc gaggcgacga gctgcacggg | 360 |
| ccaggagcgc tgcagcaaca gcatcaacag caacagcaac agcagcagca gcagcagcag | 420 |
| cagcagcagc agcaacagca gcagcaacaa cagcgaccgc cacatctggt gcaccacgct | 480 |
| gccaaccacc atcccgggcc cggggcatgg cggagtgcgg cggctgcagc tcacctccct | 540 |
| ccctccatgg gagcttccaa cggcggtttg ctctattcgc agccgagctt cacggtgaac | 600 |
| ggcatgctgg gcgcaggagg gcagccggct gggctgcacc accacggcct gagggacgcc | 660 |
| cacgatgagc cacaccatgc agaccaccac ccgcatccgc actctcaccc acaccagcaa | 720 |
| ccgcccccgc cacctccccc acaaggccca ccgggccacc caggcgcgca ccacgacccg | 780 |
| cactcggacg aggacacgcc gacctcagac gacctggagc agttcgccaa gcaattcaag | 840 |
| cagaggcgga tcaaactcgg atttactcaa gcagacgtgg ggctggcgct tggcaccctg | 900 |
| tacggcaacg tgttctcgca gaccaccatc tgcaggtttg aggccctgca gctgagcttc | 960 |
| aagaacatgt gcaagctgaa gcctttgttg aacaagtggt tggaagaggc agactcatcc | 1020 |
| tcgggcagcc ccaccagcat agacaagatc gcagcgcaag ggcgcaaacg gaaaaagcgg | 1080 |
| acctccatcg aggtgagcgt caaggggct ctggagagcc atttcctcaa atgccctaag | 1140 |
| ccctcggccc aggagatcac ctccctcgcg gacagcttac agctggagaa ggaggtggtg | 1200 |
| agatttggt tttgtaacag gagacagaaa gagaaaagga tgaccctcc cggagggact | 1260 |
| ctgccgggcg ccgaggatgt gtatgggggt agtagggaca cgccaccaca ccacggggtg | 1320 |
| cagacgcccg tccagcaggg aggcgtcctg ggtggaggca gttccaacca gcagcagcaa | 1380 |
| atacagctgc agcagttaca gatggagaag gagagactgc ggttgaaaca acaggaatta | 1440 |
| tttcggcagg caatacggaa tatcaatccc agcacagcaa atgctccaaa atgtcaggaa | 1500 |
| ttagctctgc gcagccagtt gcctacactg gagcaggatg gagggactcc gaatgcagtg | 1560 |
| tcttctcctg ggatgtctca ggaattgaga acaatgacaa ccaatagttc cgatcccttt | 1620 |
| cttaacagtg gcacctatca ctctcgagat gagagcacag acagcggcct cagcatgagc | 1680 |
| agctacagca tccctcggac cccagacgac ttcctcaaca gtgtggatga atggataca | 1740 |
| ggagacacca tcagccaaag caccctgccg tcacagcaga gccgcttccc cgactacctg | 1800 |
| gaagccctcc ctgggacaaa tgtggacctt ggcacactgg aaggagatgc aatgaacata | 1860 |
| gaaggggagg agctgatgcc cagtctgcag gaagcgctga gttccgaaat cttggacgtg | 1920 |
| gagtctgtgt ggctgccac caagctagat aaagaaagct ttctcacgtg gttatag | 1977 |

<210> SEQ ID NO 57
<211> LENGTH: 1965
<212> TYPE: DNA
<213> ORGANISM: Artificial Sequence
<220> FEATURE:
<223> OTHER INFORMATION: Nucleotide sequence encoding fusion protein of Gata4 and transactivation domain of YAP

<400> SEQUENCE: 57

| | |
|---|---|
| atgtaccaaa gcctggccat ggccgccaac cacggccccc cgcccggcgc ctacgaagca | 60 |
| ggtggccctg gcgccttcat gcacagcgcg ggcgccgcgt cctcgcccgt ctacgtgccc | 120 |
| actccgcggg tgccgtcctc tgtgctgggc ctgtcctacc tgcagggcgg tggcagtgcc | 180 |

```
gctgcagctg gaaccacctc gggtggcagc tccggggccg gcccgtcggg tgcagggcct      240
gggacccagc agggtagccc tggctggagc caagctggag ccgagggagc cgcctacacc      300
ccgccgcccg tgtccccgcg cttctctttc ccggggacta ctgggtccct ggcggccgct      360
gccgccgctg ccgcagcccg ggaagctgca gcctacggca gtggcggcgg ggcggcgggc      420
gctggtctgg ctggccgaga gcagtacggg cgtccgggct tcgccggctc ctactccagc      480
ccctacccag cctacatggc cgacgtggga gcatcctggg ccgcagccgc tgccgcctct      540
gccggcccct tcgacagccc agtcctgcac agcctgcctg gacgggccaa ccctggaaga      600
caccccaatc tcgatatgtt tgatgacttc tcagaaggca gagagtgtgt caattgtggg      660
gccatgtcca ccccactctg gaggcgagat gggacgggac actacctgtg caatgcctgt      720
ggcctctatc acaagatgaa cggcatcaac cggcccctca ttaagcctca gcgccgcctg      780
tccgcttccc gccgggtagg cctctcctgt gccaactgcc agactaccac caccacgctg      840
tggcgtcgta atgccgaggg tgagcctgta tgtaatgcct gcggcctcta catgaagctc      900
catggggttc ccaggcctct tgcaatgcgg aaggagggga ttcaaaccag aaaacggaag      960
cccaagaacc tgaataaatc taagacgcca gcaggtcctg ctggtgagac cctccctccc     1020
tccagtggtg cctccagcgg taactccagc aatgccacta gcagcagcag cagcagtgaa     1080
gagatgcgcc ccatcaagac agagcccggg ctgtcatctc actatgggca cagcagctcc     1140
atgtcccaga cattcagtac tgtgtccggc acgggccct ccatccatcc agtgctgtct      1200
gctctgaagc tgtccccaca aggctatgca tctcctgtca ctcagacatc gcaggccagc     1260
tccaagcagg actcttggaa cagcctggtc ctggctgaca gtcatgggga cataatcacc     1320
gcgcagggag gcgtcctggg tggaggcagt tccaaccagc agcagcaaat acagctgcag     1380
cagttacaga tggagaagga gagactgcgg ttgaaacaac aggaattatt tcggcaggca     1440
atacggaata tcaatcccag cacagcaaat gctccaaaat gtcaggaatt agctctgcgc     1500
agccagttgc ctacactgga gcaggatgga gggactccga atgcagtgtc ttctcctggg     1560
atgtctcagg aattgagaac aatgacaacc aatagttccg atcccttttct taacagtggc     1620 acctatcact ctcgagatga gagcacagac agcggcctca gcatgagcag ctacagcatc     1680
cctcggaccc cagacgactt cctcaacagt gtggatgaaa tggatacagg agacaccatc     1740
agccaaagca ccctgccgtc acagcagagc cgcttccccg actacctgga gccctccct     1800 gggacaaatg tggaccttgg cacactggaa ggagatgcaa tgaacataga aggggaggag     1860
ctgatgccca gtctgcagga agcgctgagt tccgaaatct tggacgtgga gtctgtgttg     1920
gctgccacca agctagataa agaaagcttt ctcacgtggt tatag                    1965
```

<210> SEQ ID NO 58
<211> LENGTH: 2040
<212> TYPE: DNA
<213> ORGANISM: Artificial Sequence
<220> FEATURE:
<223> OTHER INFORMATION: Nucleotide sequence encoding fusion protein of
      Mef2c and transactivation domain of YAP

<400> SEQUENCE: 58

```
atggggagaa aaaagattca gattacgagg ataatggatg agcgtaacag acaggtgact       60
tttacgaaga ggaaatttgg attgatgaag aaggcttatg agctgagcgt gctgtgcgac      120
tgtgagattg cactgatcat cttcaacagc accaacaagc tgttccagta cgccagcact      180
gacatggata aggtgttgct caagtacacc gagtacaacg agccgcacga gagccggaca      240
```

```
aactcagaca ttgtggagac attgagaaag aagggcctca atggctgtga cagcccagat    300
cccgatgcag acgattcagt aggtcacagc cctgagtctg aggacaagta caggaaaatt    360
aacgaagata ttgatctaat gatcagcagg caaagattgt gtgctgttcc acctcccagc    420
tttgagatgc cagttaccat cccagtgtcc agccataaca gtttggtgta cagcaatcct    480
gtcagcacac tgggaaaccc caatcttctg ccactggccc acccgtctct gcagaggaat    540
agtatgtctc ctggtgtaac acatagacct ccaagtgcag gtaacacagg cggtctgatg    600
ggcggagatc tgacatccgg tgcaggcacc agcgcaggga atggatacgg caaccccgg    660 aactcaccag gcctgctggt ctcacctggt aacctgaaca agaatataca agccaaatct    720
cctcccccta tgaatctagg aatgaataat cgtaagccag atctccgcgt tcttatccca    780
cctggcagca agaacacgat gccatcagtg aatcaaagga taaataactc ccagtcggct    840
cagtcattgg ctaccccggt ggtttccgta gcaactccta ctttaccagg acaaggaatg    900
ggaggatatc catcagccat tcaacaaca tatggtactg agtactctct gagtagcgca    960
gatctgtcat ctctgtctgg cttcaacact gccagtgcgc tccacctcgg ctctgtaact   1020
ggctggcagc agcagcacct acataacatg ccgccatctg ccctcagtca gttgggagct   1080
tgcactagca ctcatttatc tcagagttca aatctctccc tgccttctac tcaaagcctc   1140
agcatcaagt cagaacctgt ttctcctcct agagaccgta ccaccacccc ttcgagatac   1200
ccacaacaca ccacgcgcca cgaggcgggg aggtctcctg ttgacagctt gagcagctgt   1260
agcagttcct acgatgggag cgaccgagag gatcaccgga acgaattcca ctcccccatt   1320
ggactcacca gaccttcgcc ggacgaaagg gaaagtcctt cagtcaagcg catgcgactc   1380
tctgaaggat gggcaacaca gggaggcgtc ctgggtggag gcagttccaa ccagcagcag   1440
caaatacagc tgcagcagtt acagatggag aaggagagac tgcggttgaa acaacaggaa   1500
ttatttcggc aggcaatacg gaatatcaat cccagcacag caaatgctcc aaaatgtcag   1560
gaattagctc tgcgcagcca gttgcctaca ctggagcagg atggagggac tccgaatgca   1620
gtgtcttctc ctgggatgtc tcaggaattg agaacaatga caaccaatag ttccgatccc   1680
tttcttaaca gtggcaccta tcactctcga gatgagagca cagacagcgg cctcagcatg   1740
agcagctaca gcatccctcg gacccagac gacttcctca acagtgtgga tgaaatggat   1800
acaggagaca ccatcagcca aagcaccctg ccgtcacagc agagccgctt ccccgactac   1860
ctggaagccc tccctgggac aaatgtggac cttggcacac tggaaggaga tgcaatgaac   1920
atagaagggg aggagctgat gcccagtctg caggaagcgc tgagttccga aatcttggac   1980
gtggagtctg tgttggctgc caccaagcta gataaagaaa gctttctcac gtggttatag   2040
```

<210> SEQ ID NO 59
<211> LENGTH: 2196
<212> TYPE: DNA
<213> ORGANISM: Artificial Sequence
<220> FEATURE:
<223> OTHER INFORMATION: Nucleotide sequence encoding fusion protein of
      Tbx5 and transactivation domain of YAP

<400> SEQUENCE: 59

```
atggccgata cagatgaggg ctttggcctg gcgcgcacgc tctctggagcc tgattccaaa     60 gacaggtctt gcgattcgaa acctgagagt gctctggggg ctcccagcaa gtctccatca    120
tccccgcagg ctgccttcac ccagcagggc atgaaggaa tcaaggtgtt tcttcatgaa    180
cgtgaactgt ggctgaagtt ccacgaagtg ggcacagaga tgatcatcac caaggcaggg    240
```

```
aggagaatgt tccctagtta caaagtgaag gtgactggcc ttaatcccaa aacgaagtat    300
attcttctca tggatattgt tcccgcagac gaccacagat ataaatttgc tgataacaaa    360
tggtccgtaa ctggcaaagc agagcctgcc atgccgggc gcctttacgt gcacccggac    420
tccccagcaa ccggagccca ctggatgcga caacttgtct ccttccagaa gctcaaactc    480
accaacaacc acctggaccc gtttggacac attatcctga actccatgca caaataccag    540
ccccgattac acatcgtgaa agcagacgaa ataatgggt tcggttcaaa gaacactgcg    600
ttttgcaccc acgtcttccc ggagacagct tttatcgctg tgacttcgta ccagaatcac    660
aagatcacac agctgaaaat tgagaacaac cccttcgcca aaggctttcg ggcagtgat     720 gacctggagt tacacaggat gtctcggatg caaagtaaag agtatcctgt ggttcccagg    780
agcacagtga ggcacaaagt cacctccaac cacagccct tcagcagcga gacccgagct    840
ctctccacct catccaattt agggtcccag taccagtgtg agaatggtgt ctctggcccc    900
tcccaggacc ttctgccccc acctaaccca tacccactgg cccaggagca cagccaaatt    960
taccactgta ccaagaggaa agatgaggaa tgttccagca cggagcaccc ctataagaag   1020
ccgtacatgg agacatcccc cagcgaggaa gacaccttct atcgctcggg ctaccccag    1080 cagcagggcc tgagtacctc ttacaggaca gagtcggccc agcggcaggc ctgcatgtat   1140
gccagctccg ctccccccag cgagcccgtg cctagcctgg aggacatcag ctgtaacaca   1200
tggcccagca tgccctccta tagcagctgt accgtcacca ccgtgcagcc catggaccgt   1260
cttccctacc agcacttctc cgctcatttc acctcggggc ccctggtccc tcggttggct   1320
ggcatggcca accatggttc tccccagctc ggcgaaggga tgtttcagca ccagacctca   1380
gtggcccatc agcctgtggt caggcagtgc gggcctcaga ctggccttca gtctccgggc   1440
ggcctccagc ccccagagtt tctctacact cacggcgtgc ccaggaccct gtcccccat    1500 cagtatcact cggtacacgg cgtcggcatg gtgccagagt ggagtgagaa tagccaggga   1560
ggcgtcctgg gtggaggcag ttccaaccag cagcagcaaa tacagctgca gcagttacag   1620
atggagaagg agagactgcg gttgaaacaa caggaattat ttcggcaggc aatacggaat   1680
atcaatccca gcacagcaaa tgctccaaaa tgtcaggaat tagctctgcg cagccagttg   1740
cctacactgg agcaggatgg agggactccg aatgcagtgt cttctcctgg gatgtctcag   1800
gaattgagaa caatgacaac caatagttcc gatcccttc ttaacagtgg cacctatcac   1860
tctcgagatg agagcacaga cagcggcctc agcatgagca gctacagcat ccctcggacc   1920
ccagacgact tcctcaacag tgtggatgaa atggatacag gagacaccat cagccaaagc   1980
accctgccgt cacagcagag ccgcttcccc gactacctgg aagccctccc tgggacaaat   2040
gtggaccttg gcacactgga aggagatgca atgaacatag aagggagga gctgatgccc   2100 agtctgcagg aagcgctgag ttccgaaatc ttggacgtgg agtctgtgtt ggctgccacc   2160
aagctagata aagaaagctt tctcacgtgg ttatag                             2196
```